(12) United States Patent
O'Neil et al.

(10) Patent No.: US 10,390,884 B2
(45) Date of Patent: Aug. 27, 2019

(54) METHODS AND TEMPLATES FOR SHAPING PATIENT-SPECIFIC ANATOMICAL-FIXATION IMPLANTS

(71) Applicant: DePuy Synthes Products, Inc., Raynham, MA (US)

(72) Inventors: Michael O'Neil, West Barnstable, MA (US); Roman Lomeli, Plymouth, MA (US); Robert Sommerich, Norton, MA (US); Mark Hall, Bridgewater, MA (US); Joseph Peterson, South Dartmouth, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 335 days.

(21) Appl. No.: 15/196,151

(22) Filed: Jun. 29, 2016

(65) Prior Publication Data
US 2017/0000568 A1    Jan. 5, 2017

Related U.S. Application Data

(60) Provisional application No. 62/186,690, filed on Jun. 30, 2015.

(51) Int. Cl.
*A61B 34/10* (2016.01)
*A61B 17/88* (2006.01)
(Continued)

(52) U.S. Cl.
CPC ............ *A61B 34/10* (2016.02); *A61B 5/4566* (2013.01); *A61B 17/8863* (2013.01);
(Continued)

(58) Field of Classification Search
CPC .......... A61B 17/8863; A61B 2034/102; A61B 2034/108; A61B 2090/061; A61B 2017/568
See application file for complete search history.

(56) References Cited

U.S. PATENT DOCUMENTS 3,365,804 A    1/1968  Gottfrid et al.
5,257,184 A   10/1993  Mushabac
(Continued)

FOREIGN PATENT DOCUMENTS

WO    WO 2009/124245    10/2009

OTHER PUBLICATIONS http://www/nuvasive.com/news/nuvasive-to-exhibit-game-changing-new-products-and-procedures-at-the-28th-annual-american-spine-society-annual-meeting/; webpage accessed Oct. 21, 2016, 3 pgs.
(Continued)

*Primary Examiner* — Nicholas W Woodall
(74) *Attorney, Agent, or Firm* — BakerHostetler

(57) ABSTRACT

In one embodiment, an anatomical implant template has a template body having opposed first and second terminal ends. The template body bends so as to change the body from a first configuration, whereby the body extends from the first terminal end to the second terminal end along a first path, to a second configuration, whereby the body extends from the first terminal end to the second terminal end along a second path, different from the first path, the second path conforming more closely to the curvature of the at least one anatomical body. The body supports at least one device that outputs at least one signal from which a shape of the body in the second configuration can be ascertained. The anatomical implant template can further communicate the at least one signal to a computing device that generates signals for bending an anatomical implant.

16 Claims, 9 Drawing Sheets

(51) Int. Cl.
- *A61B 17/56* (2006.01)
- *A61B 90/98* (2016.01)
- *A61B 5/00* (2006.01)
- *A61B 90/00* (2016.01)
- *A61B 17/00* (2006.01)

(52) U.S. Cl.
CPC .... *A61B 90/98* (2016.02); *A61B 2017/00221* (2013.01); *A61B 2017/568* (2013.01); *A61B 2034/108* (2016.02); *A61B 2090/061* (2016.02)

(56) References Cited

U.S. PATENT DOCUMENTS

| | | | |
|---|---|---|---|
| 5,992,210 | A | 11/1999 | Blurton-Jones |
| 6,035,691 | A | 3/2000 | Lin et al. |
| 6,260,395 | B1 | 7/2001 | Webster |
| 6,578,280 | B2 | 6/2003 | Kinoshita et al. |
| 6,823,234 | B2 | 11/2004 | Otsuki et al. |
| 7,454,939 | B2 | 11/2008 | Garner et al. |
| 8,177,843 | B2 | 5/2012 | Schalliol |
| 8,607,603 | B2 * | 12/2013 | Justis ........... A61B 17/8863 140/123 |
| 8,773,650 | B2 | 7/2014 | Froggatt et al. |
| 2002/0038163 | A1 | 3/2002 | Hazama |
| 2003/0096210 | A1 | 5/2003 | Rubbert et al. |
| 2004/0122549 | A1 | 6/2004 | Otsuki et al. |
| 2005/0262911 | A1 | 12/2005 | Dankowicz et al. |
| 2006/0150698 | A1 | 7/2006 | Garner et al. |
| 2006/0150699 | A1 | 7/2006 | Garner et al. |
| 2009/0249851 | A1 | 10/2009 | Isaacs |
| 2009/0254097 | A1 | 10/2009 | Isaacs |
| 2009/0254326 | A1 | 10/2009 | Isaacs |
| 2016/0175013 | A1 * | 6/2016 | Redmond ......... A61B 17/8863 72/15.3 |

OTHER PUBLICATIONS http://www.technobis.com/markets/medical/fibre-optic-sensing/; webpage accessed Nov. 29, 2016, 3 pgs.
http://www.technobis.com/files/5114/2485/2521/TFT_APPNOTE_-_Shape_Sensing_V3.pdf; webpage accessed Nov. 29, 2016, 2 pgs.
http://lunainc.com/growth-area-technology-development/optical-systems/; webpage accessed Nov. 29, 2016, 2 pgs.
Mukherjee, et al., Piezoelectric Sensor and Actuator Spatial Design for Shape Control of Piezolaminated Plates; AIAA Journal, vol. 40, No. 6, Jun. 2002, 1204-1210.
Lin, et al., Adaptive modeling and shape control of laminated plates using piezoelectric actuators; Journal of Materials Processing Technology, vol. 189, Issue 1-3, Jul. 2007, 231-236.
Agrawal, et al., Modeling and Shape Control of Piezoelectric Actuator Embedded Elastic Plates; Journal of Intelligent Material Systems and Structures, vol. 5, Jul. 1994, 514-521.
Pilson, Thesis: Automated Manufacture of Spinal Instrumentation by Richard Ryan Pilson; Submitted to the faculty of Virginia Polytechnic Institute & State University, Feb. 6, 2006, 115 pgs.
http://research.wustl.edu/Offices_Committees/OTM/techsearch/TechPages/Pages/WUSTL012959.aspx; website accessed Nov. 29, 2016, 1 pg.
http://www.cooneymarine.co.uk/pages/tube-bending.html; webpage accessed Nov. 29, 2016, 1 pg.
http://www.core77.com/blog/digital_fabrication/inventables_launches_3d_carving_machine_on_kickstarter_reaches_funding_target_in_minutes_27808.asp#more; website accessed Nov. 29, 2016; 13 pgs.
NASA, National Aeronautics Space Administration; Fiber Optic Sensing System (FOSS) monitors multiple critical parameters in real time, Technology Solution, Jun. 2015, 4 pgs.
Irschik et al., On the Use of Piezoelectric Sensors in Structural Mechanics: Some Novel Strategies, Sensors, 2010, 5626-5641.
Langlotz, et al., A Pilot Study of Computer-Assisted Optimal Contouring of Orthopedic Fixation Devices, Computer Aided Surgery 4, 305-313, 1999.
http://www.polytec.com/fileadmin/user_uploads/Products/Faseroptische_Sensorik/documents/PH_TFT_APPNOTE_-_Shape_Sensing.pdf, webpage accessed Dec. 2, 2016, 2 pgs.
Luna Innovations Incorporated, Fiber Optic Shape Sensing, Current State of Technology, Jun. 21, 2013, 6 pages.

* cited by examiner

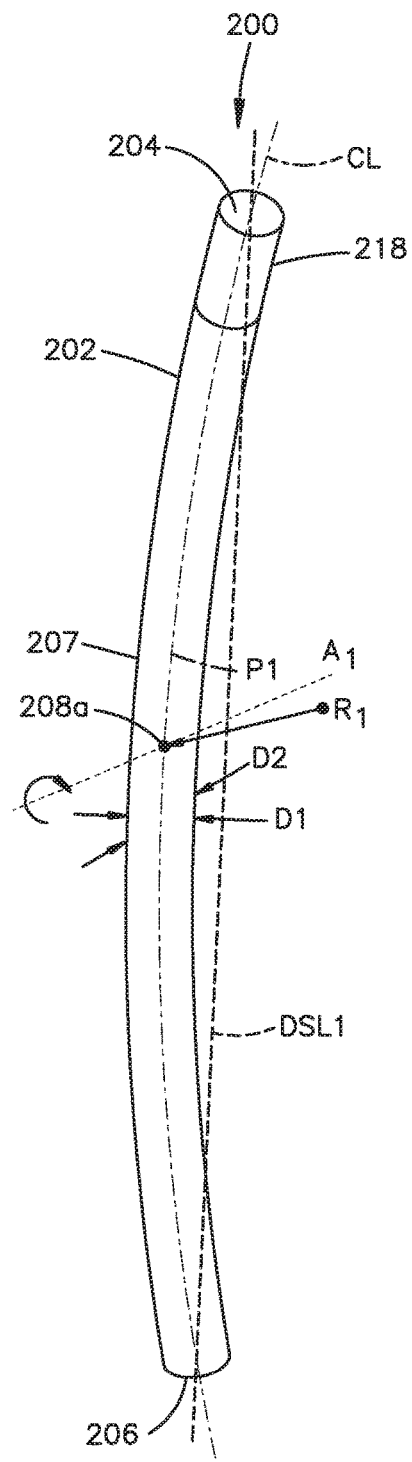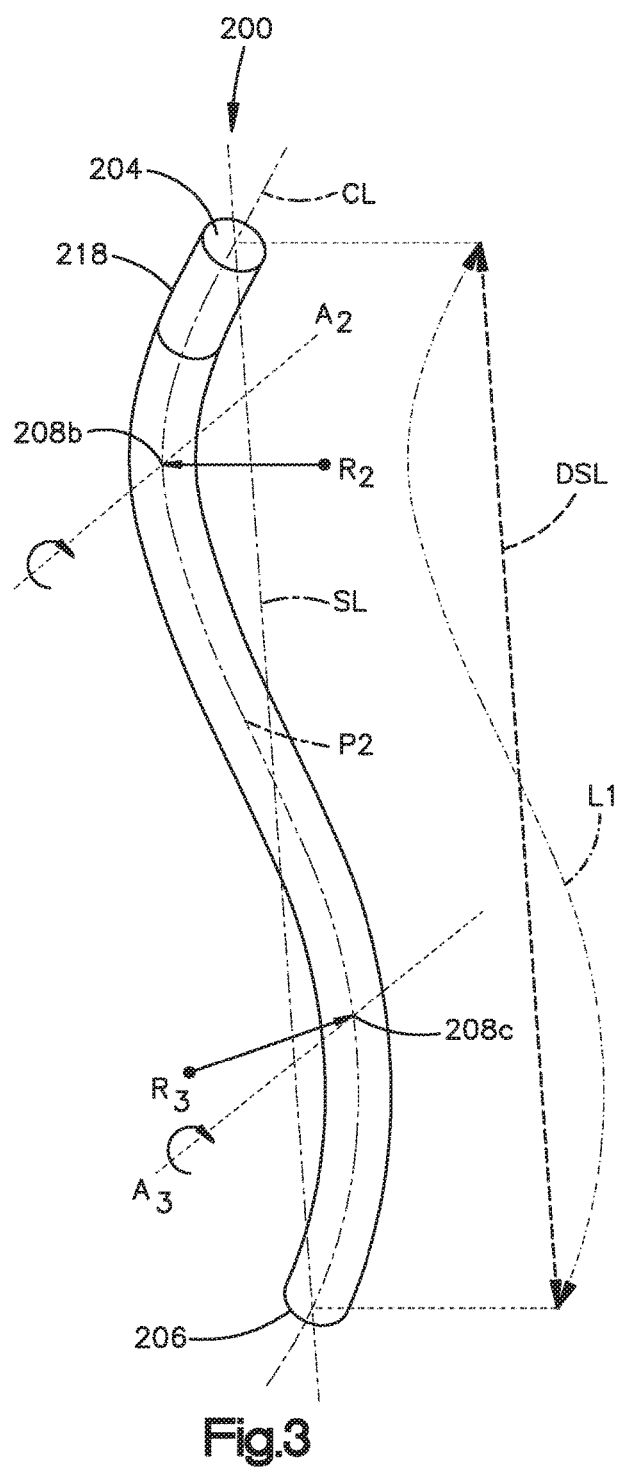
Fig.2
Fig.3

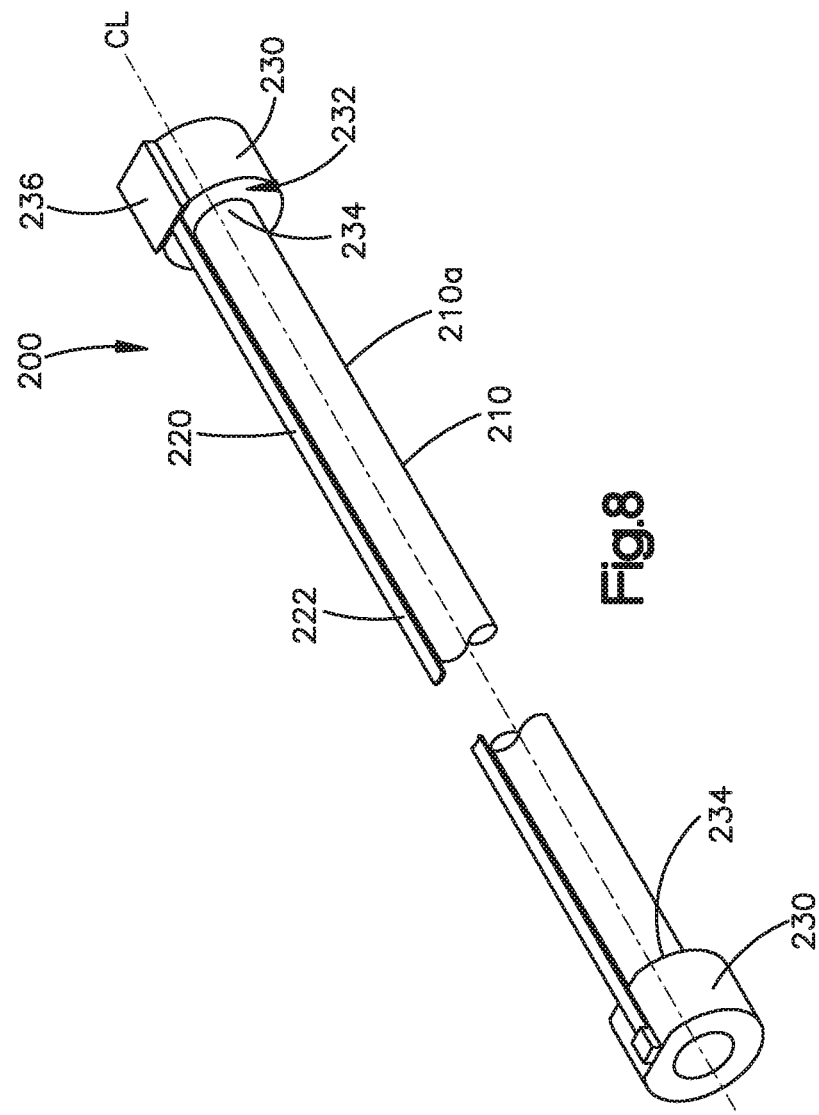

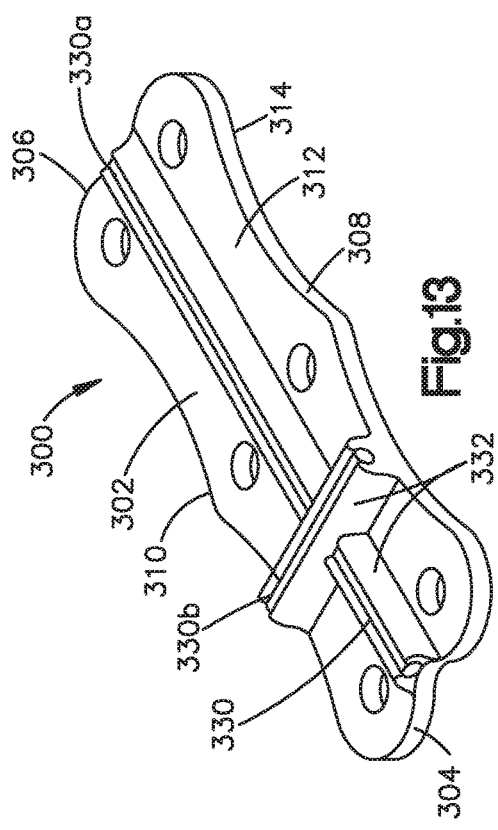
Fig.13
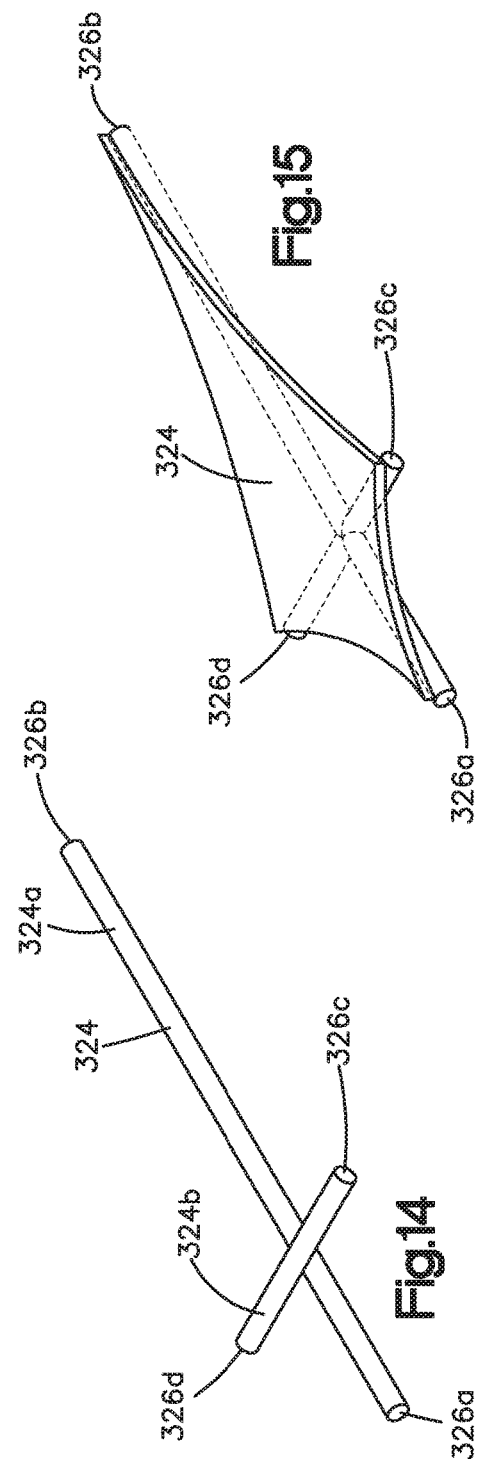
Fig.14
Fig.15

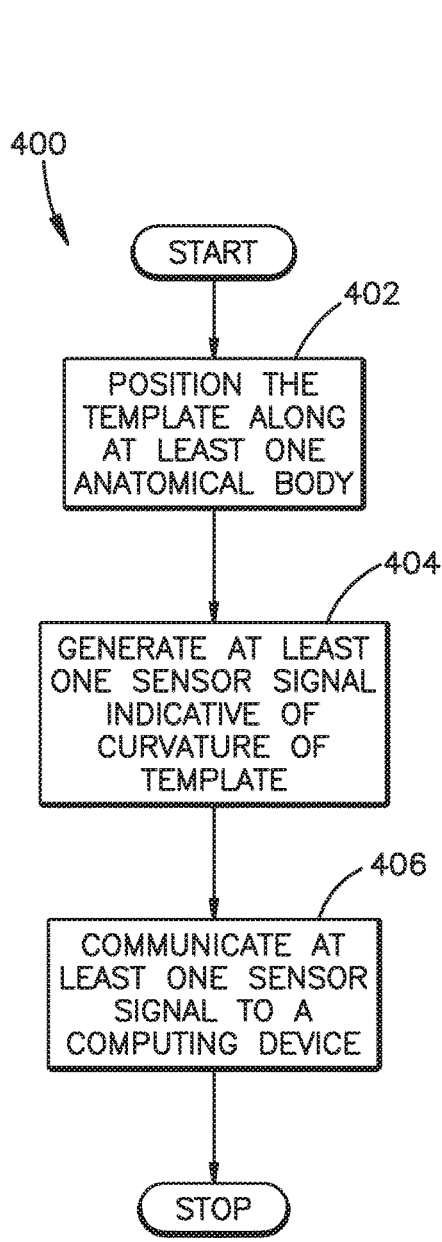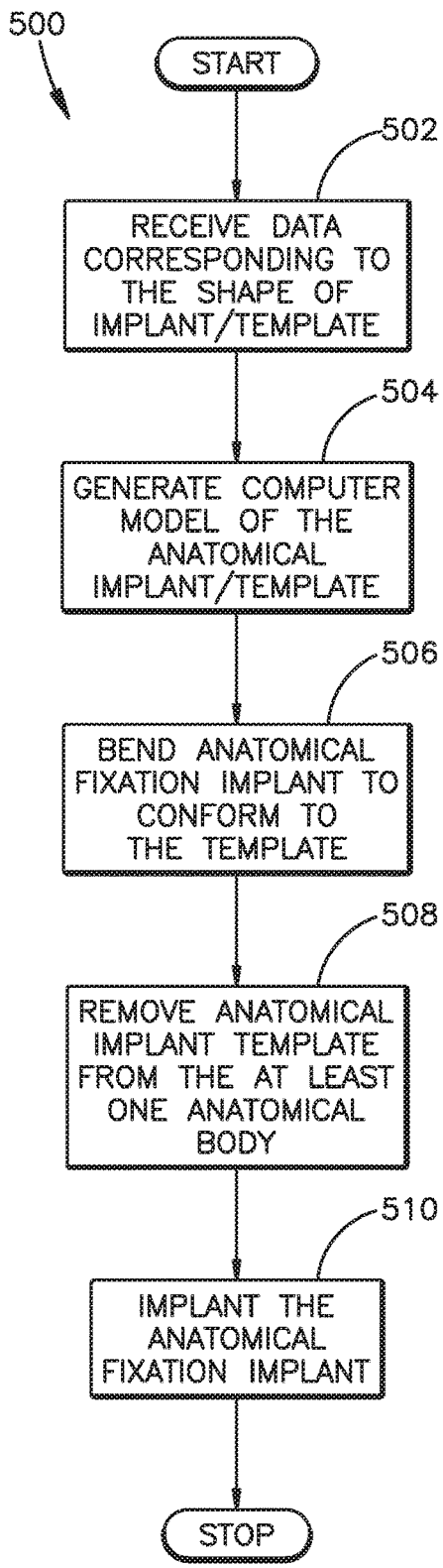
Fig.16
Fig.17

METHODS AND TEMPLATES FOR SHAPING PATIENT-SPECIFIC ANATOMICAL-FIXATION IMPLANTS

CROSS-REFERENCE TO RELATED APPLICATIONS

This application claims the benefit of U.S. Provisional Application No. 62/186,690, filed Jun. 30, 2015, the contents of which are hereby incorporated by reference as if set forth in their entirety herein.

BACKGROUND

Spinal fusion involves joining two or more adjacent vertebrae with an anatomical-fixation implant, and more specifically a spinal-fixation implant, to restrict movement of the vertebrae with respect to one another. For a number of known reasons, spinal-fixation implants are used in spine surgery to align and/or fix a desired relationship between adjacent vertebral bodies. Spinal-fixation implants may include, for example, fixation rods and/or fixation plates having sufficient length to span two or more vertebrae and having sufficient rigidity to maintain a fixed relationship between vertebrae under normal physiological loading of the spine. Each fixation rod and/or fixation plate may be attached to the vertebrae via various bone-fixation devices such screws, bolts, nails, hooks or the like, that pass through the rods and/or plates into the vertebrae, or may be attached to the vertebrae via various bone-fixation devices that are attached to the vertebrae before receiving the fixation rods and/or plates, such as bone anchor assemblies having anchor seats with rod-receiving channels.

Typically, the spinal-fixation implant is provided to the surgeon in a first (e.g., initial or pre-operative) configuration, and must be bent during surgery to a second (e.g., final or post-operative) configuration that is curved so as to align the spinal-fixation implant with the desired, post-operative curvature or contour of the at least one anatomical body. Before bending the spinal-fixation implant, the post-operative spinal contour is determined or approximated using a relatively malleable implant template as a guide or pattern. The implant template has a shape or form such as a rod and/or plate that is similar to the form of the spinal-fixation implant, although the curvature of the implant template initially might not match that of the spinal-fixation implant. The implant template also has a rigidity that is less than that of the spinal-fixation implant. Consequently, unlike the spinal fixation implant, the implant template can be bent by hand. However, due to the ease with which the implant template can be bent, the implant template itself is not suitable for use as a spinal-fixation implant as the implant template would not maintain a fixed relationship between vertebrae under normal physiological loading of the spine.

In operation, the implant template is positioned into the target area of the spine, and the implant template is bent by hand from an initial contour to the desired final or post-operative contour. Upon achieving the final spinal contour, the implant template is removed from the spine, and the spinal-fixation implant is bent using a manual hand-operated bending tool so as to match the post-operative contour of the implant template. As the spinal-fixation element is bent, the surgeon holds the spinal-fixation implant and the implant template adjacent to one another so as to compare the contour of the spinal-fixation implant with the final contour of the implant template. The surgeon continues this process of bending the spinal-fixation implant and comparing it with the implant template until the final contour is achieved. The bending can be performed in multiple steps so as to obtain one or more intermediate contours between the initial contour and the final contour. Once the final contour is achieved, the spinal-fixation implant is implanted into the spine by attaching the spinal-fixation implant to the vertebrae.

BRIEF DESCRIPTION OF THE DRAWINGS

The foregoing summary, as well as the following detailed description of embodiments of the application, will be better understood when read in conjunction with the appended drawings. For the purposes of illustrating the methods and devices of the present application, there is shown in the drawings representative embodiments. It should be understood, however, that the application is not limited to the precise methods and devices shown. In the drawings:

FIG. 2 shows a perspective side view of an anatomical implant template according to one embodiment in a first configuration;

FIG. 3 shows a perspective side view of the anatomical implant template of FIG. 2 in a second configuration;

FIG. 8 shows an exploded perspective end view of the anatomical implant template of FIGS. 2 and 3 according to another embodiment;

FIG. 13 shows a perspective view of the anatomical implant template of FIGS. 9 and 10 according to yet another embodiment;

FIG. 14 shows a perspective view of the at least one sensor of FIG. 13 according to one embodiment;

FIG. 15 shows a perspective view of the at least one sensor of FIG. 13 according to another embodiment;

FIG. 16 shows a simplified flow diagram of a method of operating the anatomical implant template of FIG. 1 according to one embodiment; and FIG. 17 shows a simplified flow diagram of a method of manipulating the anatomical-fixation implant of FIG. 1 according to one embodiment.

DETAILED DESCRIPTION

Figure 1:
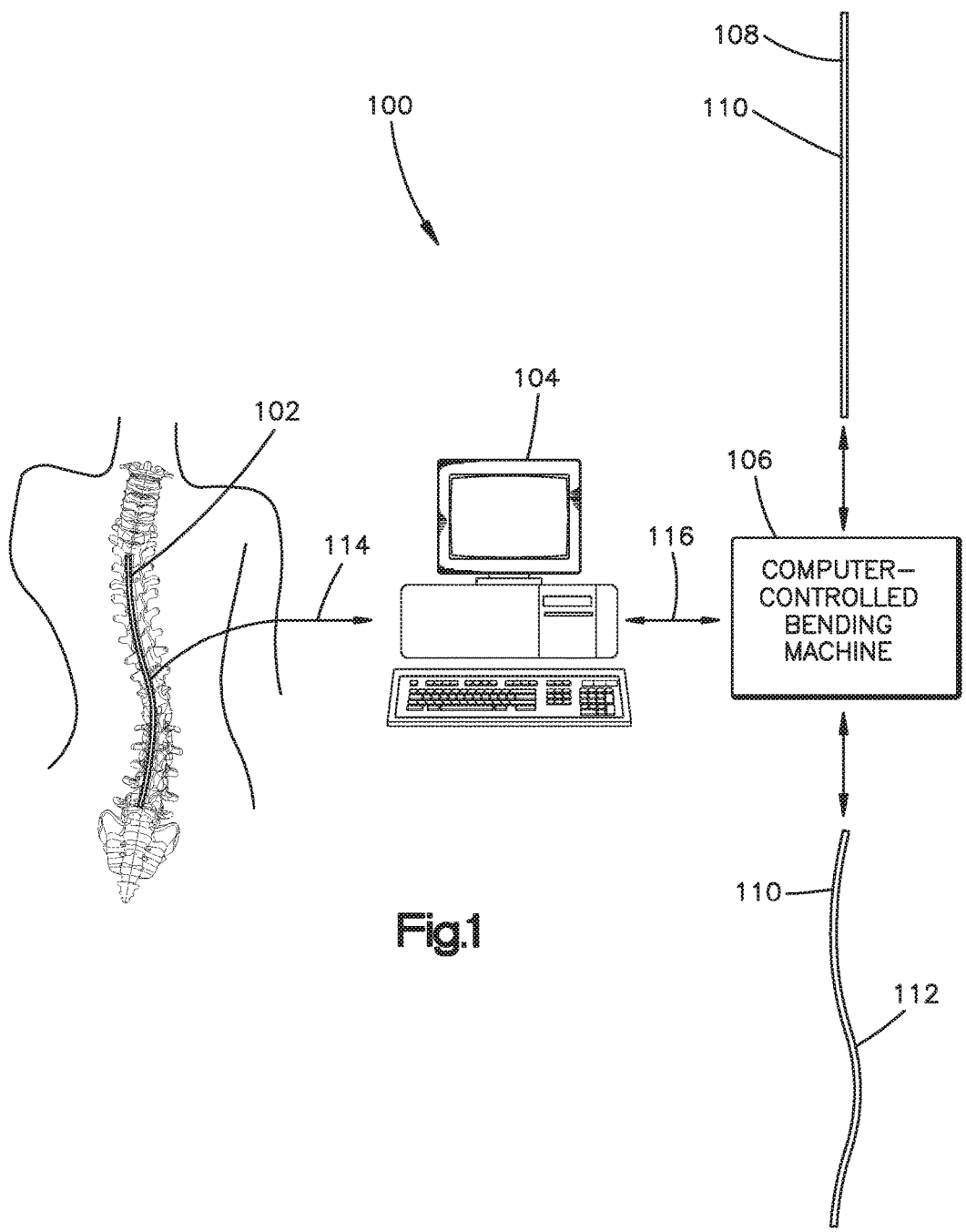
FIG. 1 shows a simplified schematic diagram of a system according to one embodiment configured to bend an anatomical-fixation implant to conform to a curvature of at least one anatomical body.

Certain terminology is used in the following description for convenience only and is not limiting. The words "right", "left", "lower" and "upper" designate directions in the drawings to which reference is made. The words "inner" and "outer" refer to directions toward and away from, respectively, the geometric center of the bone screw and related parts thereof. The terminology includes the above-listed words, derivatives thereof and words of similar import.

The technique of manually bending the spinal-fixation implant by comparing the spinal-fixation implant to an implant template as described above in the background section can have several drawbacks. For instance, bending the spinal-fixation implant in such a manner can result in operator error in trying to match the spinal-fixation implant to the implant template such that the bent spinal-fixation implant includes bends that do not adequately match the bends of the implant template. Attempting to remove or correct these incorrectly-formed bends can result in over bending of the spinal-fixation implant, which can weaken the spinal-fixation implant. Moreover, incorrectly-formed bends can be difficult, if not impossible, to remove completely.

Therefore, there is a need for improved tools and methods for bending spinal-fixation implants, and similarly for bending anatomical-fixation implants other than those used in the spine, such as orthopedic implants, cranio-maxillo-facial implants, dental implants, and other implants that are intra-operatively shaped to fit the anatomy. Although the following example embodiments pertain specifically to spinal-fixation implants, it will be understood that, unless explicitly stated otherwise, the tools and methods described herein may be used for bending anatomical-fixation implants other than spinal-fixation implants, including implants used in locations other than in the spine.

Referring to the schematic of FIG. 1, a system 100 is shown that is configured to bend an anatomical-fixation implant 110 so as to conform the anatomical-fixation implant 110 to a curvature of at least one anatomical body, and preferably, to a desired post-operative curvature of the at least one anatomical body. The anatomical-fixation implant 110 can include a body defining (without limitation) a rod, a plate, a shape having at least one rod-shaped portion and at least one plate-shaped portion, or any other shape suitable for fixing a position of one or more anatomical bodies. Further, the anatomical-fixation implant 110 has a length sufficient to extend at least from a first vertebra to a second vertebra. The at least one anatomical body can include any anatomical body having a curvature, including (without limitation) one or more of a long bone, a vertebra, at least a portion of a spinal column, and bones spanning a joint such as the wrist or ankle. The at least a portion of a spinal column can include a plurality of vertebrae up to an entirety of a spinal column, and can also include one or both of a skull and a sacrum. The curvature of the at least one anatomical body can be defined by at least one exterior surface of the at least one anatomical body. Alternatively or additionally, the curvature of the at least one anatomical body can be defined by at least one of an interior surface of the at least one anatomical body such as an intramedullary canal.

System 100 includes an anatomical implant template 102 and a computing device 104 that is in wired and/or wireless communication with the anatomical implant template 102. The anatomical implant template 102 is used as a guide or pattern to bend the anatomical-fixation implant 110 so as to conform the anatomical-fixation implant 110 to the curvature of the anatomical implant template 102. In general, the anatomical implant template 102 can be selected to have a form that corresponds to the form of the anatomical-fixation implant 110. For example, if the anatomical-fixation implant 110 defines a rod such as a spinal rod, then the anatomical implant template 102 can also define a rod. In such a case, the anatomical implant template 102 can be chosen such that the width, thickness, and/or diameter of the anatomical implant template 102 is equal to, or substantially equal to, that of the anatomical-fixation implant 110. The anatomical implant template 102 can also be selected to have a length that is less than, equal to, or greater than the length of the anatomical-fixation implant 110. Similarly, when the anatomical-fixation implant 110 defines a plate, the anatomical implant template 102 can also define a plate. In such a case, the anatomical implant template 102 can have a length, width, and/or thickness that is equal to, or substantially equal to, that of the anatomical-fixation implant 110.

As will be described in further detail below, the anatomical implant template 102 has a flexible template body that can be bent by hand to a curvature of the at least one anatomical body, and preferably, to a desired post-operative curvature of the at least one anatomical body. The template body supports at least one device that outputs a signal 114 from which the curvature of the anatomical implant template 102 can be ascertained. For example, the device can be at least one sensor that outputs at least one sensor signal from which the curvature of the anatomical implant template 102 can be ascertained. Alternatively, the at least device can be a radio-frequency identification (RFID) device that outputs the signal 114 to an RFID receiver. The at least one signal 114 can be indicative of absolute position of points along the anatomical implant template 102, or can be indicative of positional change of the anatomical implant template 102 from a first configuration to a second configuration. Further, the anatomical implant template 102 is configured to communicate the at least one signal 114 to the computing device 104 via a wireless, wired, or optical connection. Thus, the at least one signal can be, for example, an electrical signal or an optical signal.

The computing device 104 is configured to receive the at least one signal 114 from the anatomical implant template 102 and generate implant bending signals 116. The computing device 104 can also generate a computer model of the shape and curvature of the anatomical implant template 102, which can in turn be used to generate the implant bending signals 116. The system 100 can further include a computer-controlled bending machine 106 that is in wired and/or wireless communication with the computing device 104. The computing device 104 can be physically integrated with the computer-controlled bending machine 106. Alternatively, the computing device can be physically separate and spaced from the computer-controlled bending machine 106, and can communicate the implant bending signals 116 to the computer-controlled bending machine 106 via a wired or wireless connection. Note that, according to various embodiments, a system can include one or more of the computing device 104, the computer-controlled bending machine 106, and the anatomical implant template 102. For example, a system can be envisioned that includes the computing device 104 and the computer-controlled bending machine 106, without the anatomical implant template 102.

The computer-controlled bending machine 106 is configured to receive the anatomical-fixation implant 110 in a first or pre-operative implant configuration 108. In at least some embodiments, the anatomical-fixation implant 110 in the pre-operative implant configuration 108 can be a piece of stock material. For example, the anatomical-fixation implant 110 can be a rod, a plate, or a body having at least one rod-shaped portion and at least one plate-shaped portion.

Further, the anatomical-fixation implant 110 can be a relatively stiff material that is not bendable by hand so as to be capable of resisting bending when implanted into the body and subjected to anatomical loading. In other words, the anatomical-fixation implant 110 can have sufficient strength to resist bending when subjected to anatomical loading. The computer-controlled bending machine 106 is configured to bend the anatomical-fixation implant 110 into a second or post-operative implant configuration 112 based on the implant bending signals, where the post-operative implant configuration 112 conforms more closely to the shape and curvature of the anatomical implant template 102, and hence more closely to the curvature of the at least one anatomical body. Bending is performed automatically by the computer-controlled bending machine 106, as opposed to manually by hand. However, in alternative embodiments, the system 100 can include a hand-operated bending device (not shown), in lieu of or in addition to the computer-controlled bending machine 106, and an operator such as a surgeon can bend the anatomical-fixation implant 110 during a surgical procedure using the hand-operated bending device. In such alternative embodiments, the computing device 104 can include a display screen or audio device configured to communicate instructions for bending the anatomical-fixation implant 110 to the user.

Referring to FIGS. 2 and 3, an anatomical implant template 200 is shown in first and second configurations, respectively, the first configuration having a first curvature and the second configuration having a second curvature, different from the first curvature. The anatomical implant template 200, which can be used to implement the template 102 of FIG. 1, includes a template body 202 that defines a rod and further includes at least one sensor (discussed further below in relation to FIGS. 4 to 8) coupled, either directly or indirectly, to the template body 202. The anatomical implant template 200 has a first terminal end surface 204, a second terminal end surface 206 spaced from the first terminal end surface 204, and an outer surface 207 that extends from the first terminal end surface 204 to the second terminal end surface 206. The first and second terminal end surfaces 204 and 206 are spaced from one another by a dimension $D_K$ that is measured along a straight line SL from the first terminal end surface 204 to the second terminal end surface 206. The dimension $D_{SL}$ is dependent on the curvature of the anatomical implant template 200, and therefore, the dimension $D_{SL}$ can vary as the curvature of the anatomical implant template 200 is changed.

The anatomical implant template 200 extends from the first terminal end surface 204 to the second terminal end surface 206 along a center line CL that extends through a substantial geometric center of the anatomical implant template 200. The anatomical implant template 200 has an outer-most or overall dimension or length L1 that is measured along the center line CL from the first terminal end surface 204 to the second terminal end surface 206. The anatomical implant template 200 also has a plurality of cross-sections along the length L1 of the anatomical implant template 200, each cross-section extending in a plane that is perpendicular to the center line CL. Each cross-section can have any suitable cross-sectional size and shape, such as (without limitation) a circle as shown, an oval, a square, or a rectangle, and the size and shape of the cross-sections may be constant along the length L1 as shown or may vary.

Each cross-section has a first outer-most or overall cross-sectional dimension D1 along a first direction that is perpendicular to the center line CL, and a second outer-most or overall cross-sectional dimension D2 along a second direction that is perpendicular to the first direction and to the center line CL. In the embodiment of FIGS. 2 and 3, each cross-section of the anatomical implant template 200 has a substantially circular shape, wherein the first cross-sectional dimension D1 and the second cross-sectional dimension D2 are an outer-most or overall diameter of the anatomical implant template 200. In other embodiments, such as anatomical implant templates that have square, rectangular, oval, or other shape, each cross-section can have a cross-sectional dimension D1 such as a width that is less than, greater than, or equal to, a second cross-sectional dimension D2 such as a thickness.

The anatomical implant template 200 is elongate along the center line CL. Thus, the length L1 is greater than both the first and second cross-sectional dimensions D1 and D2. The length L1 is independent of the curvature of the anatomical implant template 200, and therefore, the length L1 remains constant as the curvature of the anatomical implant template 200 is changed. Further, the length L1 can have any suitable value. For example, in embodiments wherein the anatomical implant template 200 is used in a spine, the anatomical implant template 200 can have a length L1 that extends across at least two anatomical bodies such as across at least two vertebrae or across at least one vertebrae and the skull or sacrum. The first and second cross-sectional dimensions D1 and D2 can be a size suitable for attaching to the at least one anatomical body. For example, the anatomical implant template 200 can define first and second cross-sectional dimensions D1 and D2 that are suitable for installation into a rod-receiving recess of each of one or more bone anchor assemblies where the bone anchor assemblies are used to affix the anatomical-fixation implant to a spine.

The anatomical implant template 200 is configured to bend along the center line CL at one or more bending locations between the first terminal end surface 204 and the second terminal end surface 206. In at least some embodiments, the anatomical implant template 200 bends along at least a portion, up to an entirety, of the length L1 of the anatomical implant template 200 between the first and second terminal end surfaces 204 and 206. For example, the anatomical implant template 200 can include a bending location that extends continuously along the center line CL along the at least a portion, up to an entirety, of the length L1 of the anatomical implant template 200. Alternatively, the anatomical implant template 200 can include a plurality of bending locations, each of which extends continuously along the center line CL along a different portion of the anatomical implant template 200. Alternatively still, the bending locations can be defined by discrete bending points along the center line CL along at least a portion, up to an entirety, of the length L1 of the anatomical implant template 200, where the discrete bending points are spaced from one another along the center line CL. For illustrative purposes, FIG. 3 shows the anatomical implant template 200 having two bends that combine to form an s-shape; however, the user can bend the anatomical implant template 200 can have as few as one bend or more than two bends.

The anatomical implant template 200 is configured to bend at the bending locations so as to change the anatomical implant template 200 from a first configuration, whereby the anatomical implant template 200 extends from the first terminal end surface 204 to the second terminal end surface 206 along a first path P1, to a second configuration, whereby the anatomical implant template 200 extends from the first terminal end surface 204 to the second terminal end surface 206 along a second path P2, different from the first path P1. The first and second paths P1 and P2 can be co-linear with, or extend parallel to, the center line CL. The first path P1 has a first curvature, and the second path P2 has a second curvature, different from the first curvature. In at least some embodiments, the first configuration is an initial or pre-operative configuration, and the second configuration is a subsequent or post-operative configuration, where the subsequent or post-operative configuration can conform more closely to the desired, post-operative curvature or contour of the at least one anatomical body than the initial or pre-operative configuration.

It will be understood that the first and second paths P1 and P2 shown in FIGS. 2 and 3 are merely examples and that, in practice, the first and second paths P1 and P2, and hence the first and second curvatures, can vary from that shown in FIGS. 2 and 3. The first path P1 can define a curvature such as a lordotic curvature or other curvature, or can extend along a straight line. The second path can define an s-shaped curvature as shown, a lordotic curvature, a parabolic curvature, or any other desired, post-operative curvature of the at least one anatomical body. In at least some embodiments, the anatomical implant template 200 is further configured to bend at the bending locations so as to change the template body 202 from the second configuration back to the first configuration or to a third configuration having a curvature different from both the first and second configurations.

The anatomical implant template 200 is configured to bend at each of the bending locations along the center line CL towards any direction that is perpendicular to the center line CL at the bending location. For example, the anatomical implant template 200 can bend at each bending location about a respective axis A of rotation, where each respective axis A of rotation extends through its respective bending location along a direction that is perpendicular to the center line CL at the respective bending location. Further, the template body 202 defines a radius of curvature R at each bending location.

In the configuration of FIG. 2 (i.e., the first configuration), the anatomical implant template 200 is shown with a single bend or curve that has a peak at point 208a. The anatomical implant template 200 is bent or curved about an axis $A_1$ of rotation that extends through the point 208a. Further, the anatomical implant template 200 has a first radius $R_1$ of curvature at the point 208a. In the configuration of FIG. 3 (i.e., the second configuration), the anatomical implant template 200 is shown with two bends or curves that have respective peaks at points 208b and 208c. The anatomical implant template 200 is bent or curved about respective axes $A_2$ and $A_3$ of rotation that extend through the points 208b and 208c, respectively. Further, the anatomical implant template 200 has second and third radii $R_2$ and $R_3$ of curvature at the points 208b and 208c, respectively.

In FIGS. 2 and 3, the anatomical implant template is changed from a first configuration having a single curve with a first peak 208a to a second configuration having two curves with first and second peaks 208b and 208c. The locations of the peaks 208b and 208c along the center line CL are different from the locations of the peak 208a. Further, the radii $R_2$ and $R_3$ of curvature at the peaks 208b and 208c is different from the radius $R_1$ of curvature of the peak 208a. However, it will be understood that the first and second configurations may vary from those shown. In particular, the anatomical implant template 200 can be changed from a first configuration having zero or more curves to a second configuration having at least one curve. Further, the locations of the peaks the curves along the center line CL can vary from the locations shown in FIGS. 2 and 3.

The center line CL can lie in a single plane in one or both of the first and second configurations. For example, in spine applications, the anatomical implant template 200 can be bent such that, when the anatomical implant template 200 is positioned along the spine, the center line CL lies in a single plane in the spine, where the single plane is the sagittal plane or the coronal plane. Alternatively, the anatomical implant template 200 can be bent such that the center line CL can lie in multiple planes in one or both of the first and second configurations. For example, in spine applications, the multiple planes can include one or more of the sagittal plane and the coronal plane.

Turning now to FIGS. 4 to 8, various embodiments of the anatomical implant template 200 of FIGS. 2 and 3 are shown. In each embodiment, the anatomical implant template 200 includes a template body 202 and at least one sensor 220 coupled to the template body 202. The template body 202 is configured to bend so as to change the anatomical implant template 200 from the first configuration to the second configuration. The at least one sensor 220 is configured to output at least one sensor signal from which the curvature of the anatomical implant template 200 in the second configuration can be ascertained. In at least some embodiments, the at least one sensor 220 can additionally generate the at least one sensor signal. Further, in at least some embodiments, the at least one sensor 220 can modify an input signal so as to produce a modified signal from which the curvature of the anatomical implant template 200 in the second configuration can be ascertained.

The template body 202 includes a flexible body 210 that extends along, or substantially parallel to, the center line CL between the first terminal end surface 204 and the second terminal end surface 206. The template body 202 can extend from the first terminal end surface 204 toward the second terminal end surface 206, and terminate at or before the second terminal end surface 206. Similarly, the template body 202 can extend from the second terminal end surface 206 toward the first terminal end surface 204, and terminate at or before the first terminal end surface 204. Alternatively, the template body 202 can extend along a portion or portions of the anatomical implant template 200 between the first and second terminal end surfaces 204 and 206, and terminate before one or both of the first and second terminal end surfaces 204 and 206. In other words, the template body 202 can have a first terminal end and a second terminal end. The first terminal end of the template body 202 can be coincident with the first terminal end surface 204 of the implant template 200 or can be located between the first and second terminal end surfaces 204 and 206. Similarly, the second terminal end of the template body 202 can be coincident with the second terminal end surface 204 or can be located between the first and second terminal end surfaces 204 and 206.

The flexible body 210 can include any suitable malleable material or combination of malleable materials that permits the template body 202 to be conformed to the desired post-operative contour of the at least one anatomical body. The malleable material or combination of materials may include one or more of a metal such as annealed aluminum, a metal alloy such as Nitinol, and a polymer. The flexible body 210 can include a plastically-deformable material configured to maintain the template body 202 in the second configuration. Alternatively, or in addition, the flexible body 210 can include an elastically-deformable material configured to return the template body 202 to the first configuration from the second configuration.

With continuing reference to FIGS. 2 to 8, the anatomical implant template 200 supports at least one sensor 220 along or substantially parallel to the center line CL between the first and second terminal end surfaces 204 and 206. The at least one sensor 220 is configured output at least one sensor signal from which the shape of the anatomical implant template 200 in the second configuration can be ascertained. The at least one sensor 220 can include a sensor body 222 having a first terminal sensor end, a second terminal sensor end spaced from the first terminal sensor end, and a first surface 222a, such as an external surface, that extends between the first and second terminal sensor ends. The sensor body 222 can be elongate from the first terminal sensor end to the second terminal sensor end.

The sensor body 222 can extend from the first terminal end surface 204 of the implant template 200 toward the second terminal end surface 206 of the implant template 200, and terminate at or before the second terminal end surface 206. Similarly, the sensor body 222 can extend from the second terminal end surface 206 toward the first terminal end surface 204, and terminate at or before the first terminal end surface 204. Alternatively, the sensor body 222 can extend along a portion or portions of the template body 202 between the first and second terminal end surfaces 204 and 206, and terminate before one or both of the first and second terminal end surfaces 204 and 206. In other words, the first terminal sensor end can be coincident with the first terminal end surface 204, or can be located between the first and second terminal end surfaces 204 and 206. Similarly, the second sensor end can be coincident with the second terminal end surface 204 or can be located between the first and second terminal end surfaces 204 and 206. The sensor body 222 can be coupled to the template body 202 such that at least a portion of the sensor body 222 is aligned with at least one of the bending locations along a direction that is perpendicular to the center line CL, such as along a radial direction. Accordingly, when the template body 202 is bent at the at least one bending location, the sensor body 222 is also bent at the at least one bending location.

Alternatively or in addition, the at least one sensor 220 can include a plurality of discrete sensor bodies 222 spaced from one another between the first and second terminal end surfaces 204 and 206. When discrete sensor bodies 222 are employed, changes in the shape of the template body 202 between the discrete sensors can be determined through extrapolation. In either case, the elongate sensor body 222 and/or the plurality of discrete sensor bodies 222 can be coupled to the template body 202 so as to be aligned with at least one of the bending locations such that the at least one sensor 220 bends at the at least one bending location. Alternatively, the sensor body 222 and/or the plurality of discrete sensor bodies 222 can be coupled to the template body 202 so as to be positioned between (i) at least one of the bending locations and (ii) another of the bending locations, the first terminal end surface 204, or the second terminal end surface 206 such that a position of the at least one sensor 220 changes relative to the at least one of the bending locations as the template body 202 is bent about the at least one of the bending locations.

The at least one sensor 220 can include any suitable sensor or combination of sensors that can sense the shape of the template body 202 in the second configuration. The at least one sensor 220 can be an active sensor that actively transmits a signal or a passive sensor. The at least one sensor 220 can include, for example, one or more position sensors that measure absolute position of the template body 202 in the second configuration or relative position such as displacement of the template body 202 from the first configuration to the second configuration. In at least some embodiments, the at least one sensor 220 can include one or more piezoelectric sensors. The piezoelectric sensors can be used to measure changes in or more of pressure, strain, and force, and convert these measured changes into an electrical charge that can form the at least one sensor signal.

In at least some embodiments, the at least one sensor 220 can include an optical sensor such as those used in fiber optic shape sensing. For example, the at least one sensor 220 can include an optical fiber having one or more Fiber Bragg Grating (FBG) sensors. Each FBG sensor is a series of optical filters that reflect a different wavelength or wavelengths while letting other wavelengths pass through. The FBG sensors respond to strain resulting from stress or pressure on the anatomical implant template. As the optical fiber is bent, the refractive index of the FBG sensors varies, thereby dictating which wavelengths pass through and which are reflected. These variations can then be converted to displacement data that can be used to determine the shape of the anatomical implant template.

Figure 4:
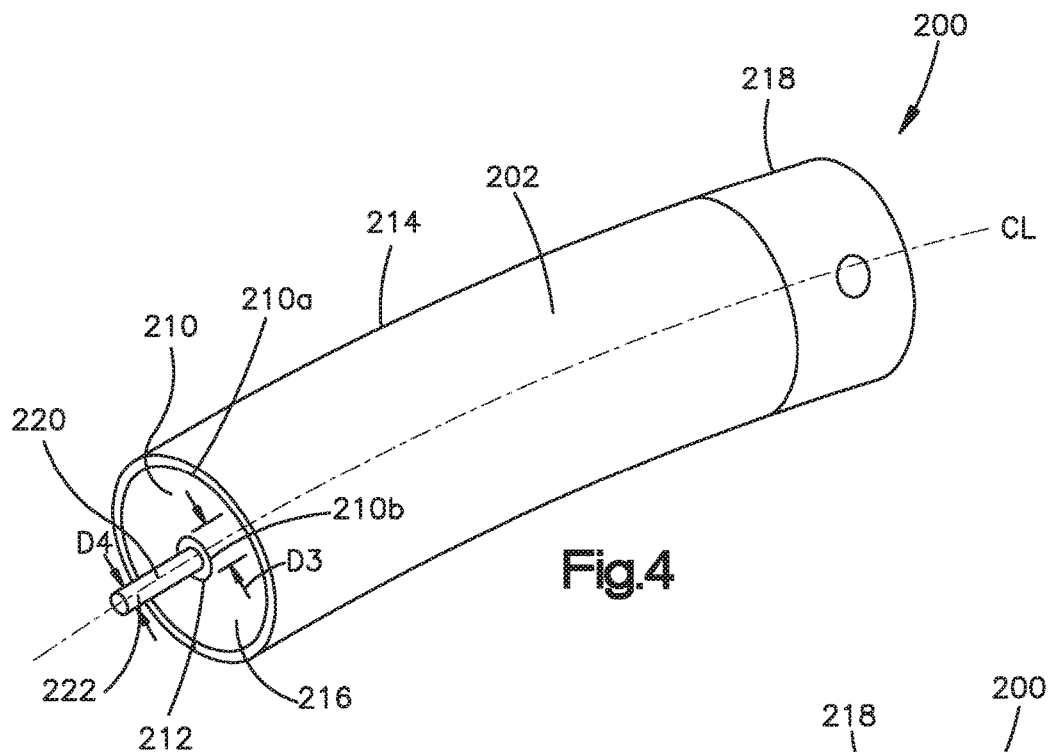
FIG. 4 shows a cross-sectional view of the anatomical implant template of FIGS. 2 and 3 according to one embodiment.

Turning now to FIG. 4, an embodiment is shown in which the template body 202 includes a flexible body 210 and can optionally include a protective covering 214. The flexible body 210 defines a tube having a first surface 210a, such as an external surface, and a second surface 210b, such as an internal surface. The internal surface 210b is spaced closer to the center line CL than the external surface 210a. Moreover, the external and internal surfaces 210a and 210b extend between the first and second terminal ends of the template body 202. The internal surface 210b defines a channel 212 that extends through an entirety or a portion of the length of the flexible body 210, and supports the at least one sensor 220. The at least one sensor 220 defines a rod having a circular cross-section, although the rod can define cross-sections having another suitable shape such as a square, rectangle, or oval.

The implant template 200 has a plurality of cross-sections along the center line CL, where each cross-section is in a plane that is perpendicular to the center line CL. In each cross-section, the external and internal surfaces 210a and 210b of the flexible body 210 can define any suitable cross-sectional shape, such as (without limitation) a circle as shown, an oval, a square, or a rectangle. Moreover, the internal surface 210b of the flexible body 210 can define a closed shape around the channel 212. In each cross-section, the internal surface 210b can define an overall dimension D3 in a plane perpendicular the center line CL, such as a diameter or width of the channel 212, where the overall dimension D3 is greater than or equal to an outer-most or overall dimension D4 of the at least one sensor 220 measured in the same plane. Thus, the channel 212 is sized and configured to receive the at least one sensor 220 therein such that the channel 212 supports the at least one sensor 220 between the first and second terminal end surfaces 204 and 206.

Figure 6:
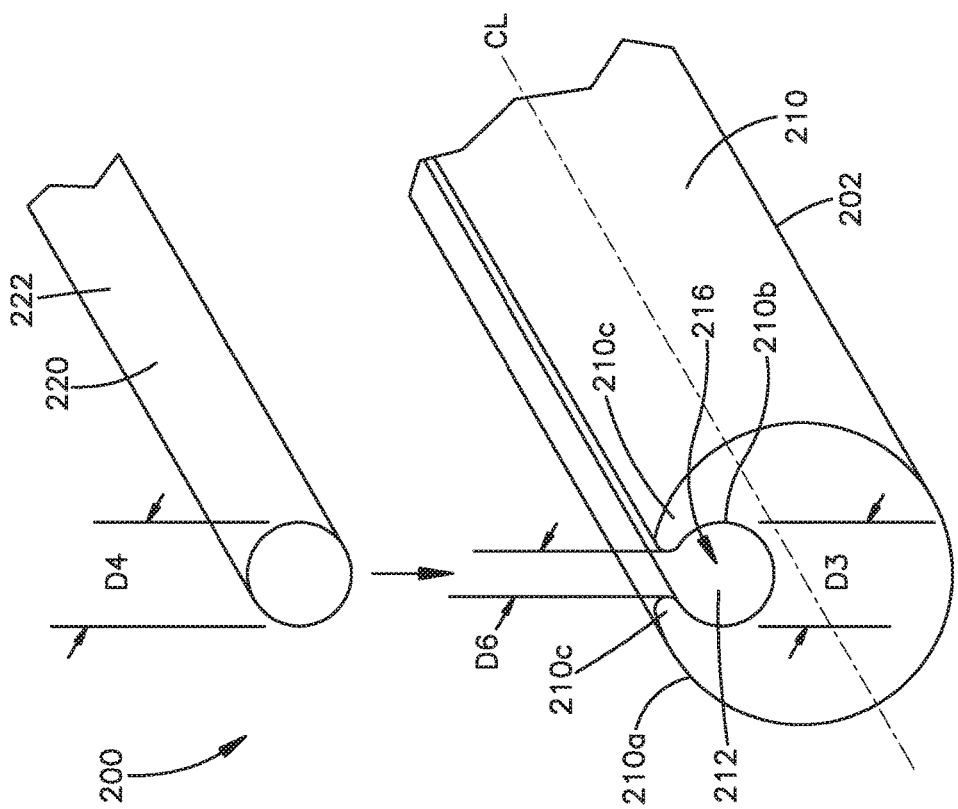
FIG. 6 shows an exploded perspective end view of the anatomical implant template of FIGS. 2 and 3 according to another embodiment.

FIG. 6 shows an alternative embodiment where the flexible body 210 defines a channel 212 that extends into the external surface 210a of the flexible body 210, such that the channel 212 is open along the external surface 210a. Thus, the flexible body 210 can define an opening 216 that is open to the channel 212, where the opening 216 has an overall dimension or width D6 along a plane that is perpendicular to the center line CL. For instance, the flexible body 210 can include a pair of opposed edges 210c that define the opening 216 therebetween. The opposed edges 210c are spaced from one another by the overall dimension D6 in a plane perpendicular to the center line CL. The overall dimension D6 can be less than, greater than, or equal to the overall dimension D4 of the at least one sensor 220. Note that the channel 212 can be radially offset from the center line CL as shown, or can be co-linear with the center line CL.

In embodiments where the overall dimension D6 of the opening 216 is less than the overall dimension D4 of the at least one sensor 220, the at least one sensor 220 can snap into the channel 212. For example, the at least one sensor 220 can compress to a dimension less than the overall dimension D4 as the at least one sensor 220 is passed through the opening 216, and then the at least one sensor 220 expand substantially back to the overall dimension D4 once the at least one sensor 220 is received in the channel 212. Alternatively, the pair of opposed edges 210c can spread apart by a distance greater than the overall dimension D6 as the at least one sensor 220 is received through the opening 216, and then the opening 216 can return substantially to the overall dimension D6 once the at least one sensor 220 is received in the channel 212. Once the at least one sensor 220 is disposed in the channel 212, the opposed edges 210c can retain the at least one sensor 220 in the channel 212.

Referring back to FIG. 4, the template body 202 can also include a protective covering 214 that covers at least a portion, up to an entirety, of the external surface 210a of the flexible body 210. The protective covering 214, if employed, can define a closed shape around the flexible body 210 in a plane perpendicular to the center line CL. The protective covering 214 can be a coating that is formed over the external surface 210a of the flexible body 210, or can be a separate sheath that is wrapped or translated over the first surface 210a of the flexible body 210.

Figure 5:
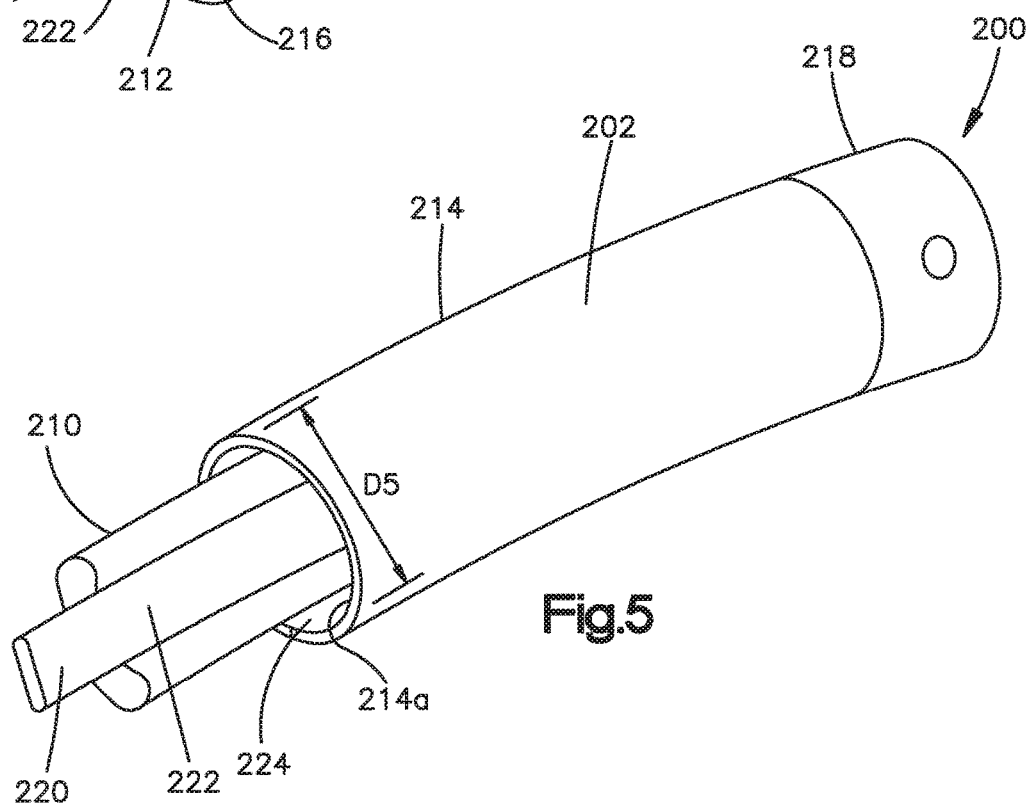
FIG. 5 shows a cross-sectional view of the anatomical implant template of FIGS. 2 and 3 according to another embodiment.

Referring to FIG. 5, an embodiment is shown in which the template body 202 includes the flexible body 210 and a protective covering 214. The flexible body 210 defines a rod or a bar having an external surface 210a that extends between the first and second terminal ends of the template body 202. The rod or bar can have a flattened cross-section as shown or another suitable cross-sectional shape. The protective covering 214 covers at least a portion of the flexible body 210 between the first and second terminal ends of the template body 202, and has an internal surface 214a that defines a channel 224 that extends at least partially through the protective covering 214. The internal surface 214a of the protective covering 214 defines an overall dimension D5, such as a diameter or width, in a plane perpendicular to the center line CL, where the overall dimension D5 is greater than a combined dimension of the flexible body 210 and the at least one sensor 220 in the same plane. Thus, the channel 224 is sized to receive both the flexible body 210 and the at least one sensor 220 such that the at least one sensor 220 is coupled to the flexible body between the flexible body 210 and at least a portion of the protective covering 214.

Figure 7:
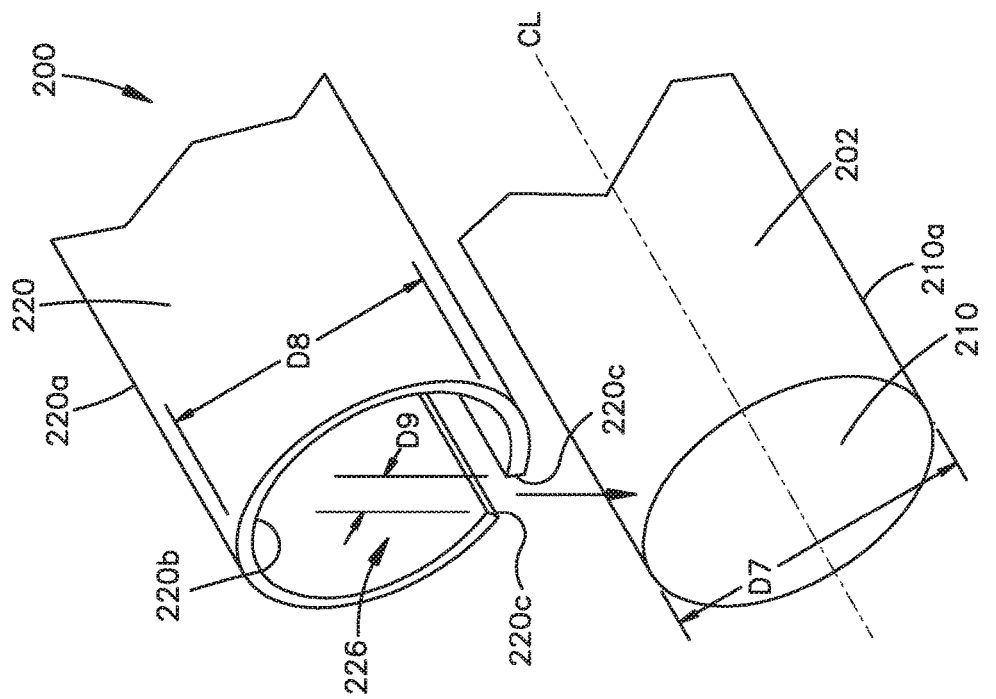
FIG. 7 shows an exploded perspective end view of the anatomical implant template of FIGS. 2 and 3 according to another embodiment.

Turning now to FIG. 7, an embodiment of an anatomical implant template 200 is shown having a flexible body 210 that can be a conventional template, and the at least one sensor 220 can be permanently coupled to, or removeably coupled to (e.g., snapped on), the flexible body 210 so as to convert the conventional template into a smart template that is configured to output at least one sensor signal from which the shape of the anatomical implant template 200 can be ascertained. In embodiments where the at least one sensor 210 is removeably coupled to the flexible body 210, the flexible body 210 can be reused after cleaning as with conventional templates. Further, the at least one sensor 210 can be disposable or can be configured to survive cleaning such that the at least one sensor 210 can be reused.

The flexible body 210 defines a rod or a bar having an external surface 210a that extends between the first and second terminal ends of the template body 202. The flexible body 210 defines a cross-sectional shape, such as (without limitation) a circle as shown, an oval, a square, or a rectangle. Moreover, in each cross-section, the flexible body 210 can have an outer-most dimension or width D7.

The at least one sensor 220 defines a tube having a first surface 220a, such as an external surface, and a second surface 220b, such as an internal surface. The internal surface 220b is spaced closer to the center line CL than the external surface 220a. The internal surface 220b defines a channel 226 that extends through an entirety or a portion of the length of the at least one sensor 220. Moreover, the external and internal surfaces 220a and 220b extend between the first and second terminal sensor ends.

The at least one sensor 220 has a plurality of cross-sections along the center line CL, where each cross-section is in a plane that is perpendicular to the center line CL. In each cross-section, the external and internal surfaces 220a and 220b of the at least one sensor 220 can define any suitable cross-sectional shape, such as (without limitation) a circle, an oval, a square, or a rectangle. In each cross-section, the internal surface 220b can define an overall dimension D8 in a plane perpendicular the center line CL, such as a diameter or width of the channel 226, where the overall dimension D8 is greater than or equal to an overall dimension D7 of the flexible body 210 measured in the same plane. Thus, the channel 226 can be sized and configured to receive the flexible body 210 therein such that the flexible body 210 supports the at least one sensor 220 between the first and second terminal end surfaces 204 and 206.

Moreover, the internal surface 220b of the at least one sensor 220 can define a closed shape around the channel 226, such that the flexible body 210 is slidably received in the channel 26. Alternatively, the at least one sensor 220 can define an open shape or a shape that is configured to open so that the at least one as sensor 220 can be wrapped around the flexible body 210 as the flexible body 210 is received into the channel 226 along a direction that is perpendicular to the center line CL. More specifically, the at least one sensor 220 can define opposed edges 220c. The opposed edges 220c can be spaced from one another so as to define an opening 228 that is open to the channel 226, where the opening 228 has an overall dimension or width D9 along a plane that is perpendicular to the center line CL. Alternatively, the opposed edges 220c can overlap one another such that the overlapping edges 220c can be separated so as to receive the flexible body 210 into the channel 226, and then can return to their overlapping state so as to retain the flexible body 210 therein.

Turning now to FIG. 8, an embodiment is shown in which the flexible body 210 defines a rod or a bar having an external surface 210a that extends between the first and second terminal ends of the template body 202. The flexible body 210 defines a cross-sectional shape, such as (without limitation) a circle as shown, an oval, a square, or a rectangle. The at least one sensor 220 can be an elongate sensor that is capable of being tensioned. In this embodiment, a single sensor 220 is shown; however, the implant template may include more than one sensor 220 spaced around the external surface 210a of the flexible body 210.

To tension the at least one sensor 220 along the flexible body 210, the implant template 200 can include at least one end cap 230, such as a pair of end caps. Each end cap 230 defines a recess 232 that is sized and shaped to receive a terminal end 234 of the flexible body 210 such that the end caps 230 are spaced from one another along the center line CL. Moreover, at least one of the end caps 230 can comprise a tensioning device such as a spring loaded tensioner 236 that applies tension to the at least one sensor 220.

Returning to FIGS. 2 and 3, the anatomical implant template 200 is configured to communicate the at least one sensor signal to a computing device such as the computing device 104 of FIG. 1 via a wired or wireless connection. The at least one sensor 220 can be configured to communicate the at least one sensor signal directly to the computing device. Alternatively, the anatomical implant template 200 can include at least one transmitter 218 coupled to the template body 202 and configured to communicate the at least one sensor signal. The at least one transmitter 218 can be coupled to the template body 202 at one of the first and second terminal end surfaces 204 and 206 or can be supported anywhere between the first and second terminal end surfaces 204 and 206. The at least one transmitter 218 can include a wireless transmitter configured to wirelessly communicate the at least one sensor signal to the computing device.

Further, the at least one transmitter 218 can include a power supply that is coupled to the template body 202, where the power supply is configured to power the at least one transmitter 218. Alternatively, the at least one transmitter 218 can be powered by a power supply that is not coupled to the template body 202, such as a power supply that is coupled to a receiver such as a radio-frequency identification (RFID) receiver, where the receiver that transmits radio energy to a device coupled to the template body 202, and the device uses the radio energy to output a response to the receiver. In the case of a wired connection, the anatomical implant template 200 can be coupled to a cable that carries the at least one sensor signal from the anatomical implant template 200 to the computing device.

Figure 10:
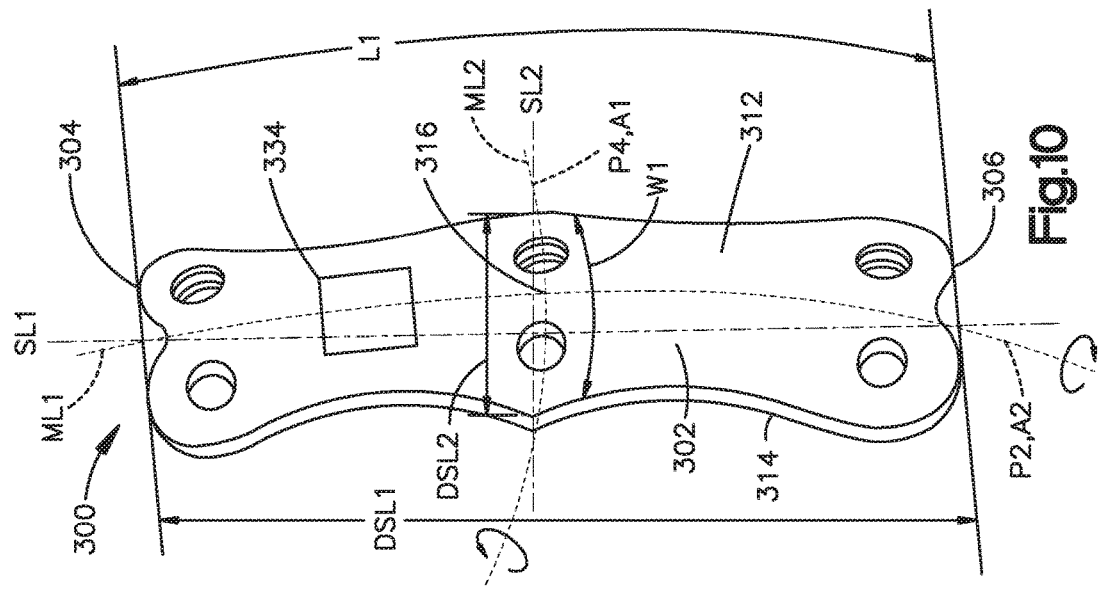
FIG. 10 shows a top perspective view of the anatomical implant template of FIG. 9 in a second configuration.
Figure 9:
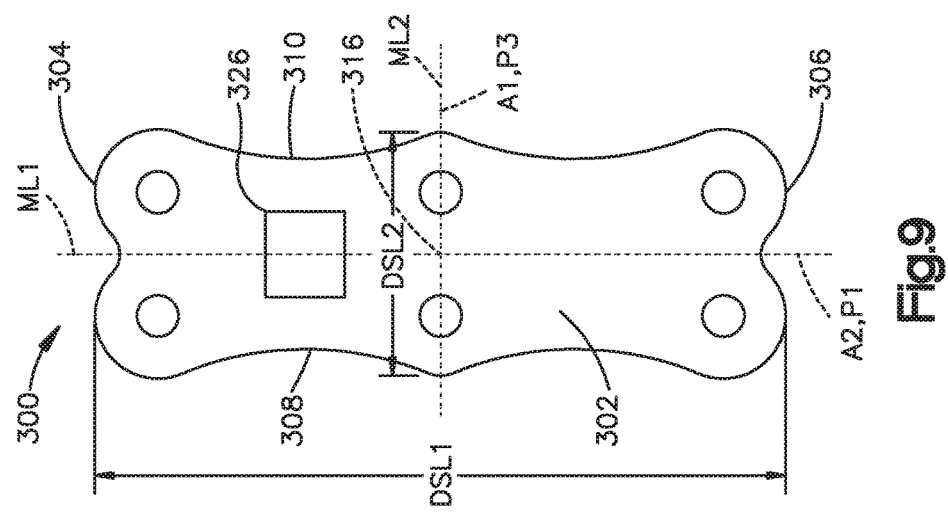
FIG. 9 shows a top perspective view of an anatomical implant template according to another embodiment in a first configuration.

Referring now to FIGS. 9 and 10, an anatomical implant template 300 according to another embodiment is shown in first and second configurations, respectively. The anatomical implant template 300, which can be used to implement the template 102 of FIG. 1, defines a plate that is configured to conform to a curvature of at least one anatomical body. The anatomical implant template 300 comprises a template body 302 and at least one sensor 324 (shown in FIGS. 11-15) coupled, either directly or indirectly, to the template body 302. The anatomical implant template 300 can also define one or more apertures 328 that extend entirely through the template body 302, each of the apertures 328 configured to receive, for example, a bone screw or pin therethrough to fix the anatomical implant template 300 to the at least one anatomical body.

The anatomical implant template 300 has a first terminal end surface 304 and an opposed second terminal end surface 306 spaced from the first terminal end surface 304. The anatomical implant 300 further has first and second opposed side surfaces 308 and 310 that extend from the first terminal end surface 304 to the second terminal end surface 306. The anatomical implant 300 yet further has opposed upper and lower surfaces 312 and 314 that extend from the first terminal end surface 304 to the second terminal end surface 306 and from the first side surface 308 to the second side surface 310. The lower surface 314 can be considered a bone-facing surface that is configured to face the at least one anatomical body when the anatomical implant template 300 is attached to the at least one anatomical body.

The anatomical implant template 300 can define an outer-most or overall dimension or length L1 that is measured along a line that extends along or parallel to the curvature of the anatomical implant template 300 from the first terminal end surface 304 to the second terminal end surface 306. For example, the length L1 can be measured parallel to a midline ML1 that extends from the first terminal end surface 304 to the second terminal end surface 306 substantially midway between the first and second side surfaces 308 and 310. The midline ML1 can also extend substantially midway between the upper and lower surfaces 312 and 314 or along one of the upper and lower surfaces 312 and 314. The length L1 is independent of the curvature of the anatomical implant template 300, and therefore, the length L1 remains constant as the curvature of the anatomical implant template 300 is changed. The anatomical implant template 300 can also have a dimension $D_{SL1}$ that is measured along a straight line SL1 from the first terminal end surface 304 to the second terminal end surface 306. The dimension $D_{SL1}$ is dependent on the curvature of the anatomical implant template 300, and therefore, the dimension $D_{SL1}$ can vary as the curvature of the anatomical implant template 300 is changed.

The anatomical template implant 300 can further define an outer-most or overall dimension or width W1 that is measured along a line that extends along or parallel to the curvature of the anatomical implant template 300 from the first side surface 308 to the second side surface 310. For example, the width W1 can be measured parallel to a midline ML2 that extends from the first side surface 308 to the second side surface 310 substantially midway between the first and second terminal end surfaces 304 and 306. The midline ML2 can also extend substantially midway between the upper and lower surfaces 312 and 314 or along one of the upper and lower surfaces 312 and 314. The width W1 is independent of the curvature of the anatomical implant template 300, and therefore, the width W1 remains constant as the curvature of the anatomical implant template 300 is changed. The anatomical implant template 300 can also have a dimension $D_{SL2}$ that is measured along a straight line SL2 from the first side surface 312 to the second side surface 314. The dimension $D_{SL2}$ is dependent on the curvature of the anatomical implant template 300, and therefore, the dimension $D_{SL2}$ can vary as the curvature of the anatomical implant template 300 is changed.

The anatomical template implant 300 can yet further define an outer-most or overall thickness T1 that is measured from the upper surface 312 to the lower surface 314. The thickness T1 is independent of the curvature of the anatomical implant template 300, and therefore, the thickness T1 remains constant as the curvature of the anatomical implant template 300 is changed. The length L1 and width W1 can be greater than the thickness T1, and in at least some embodiments, the length L1 can be greater than the width W1. The length L1, width W1, and thickness T1 of the anatomical implant template 300 can be any length L1, width W1, and thickness T1 suitable for attaching to the at least one anatomical body. For example, in embodiments wherein the anatomical implant template 300 is used in a spine, the anatomical implant template 300 can have a length L1 that is sized to extend along at least two bodies such as along at least two vertebrae or along at least one vertebra and the skull or sacrum.

The anatomical implant template 300 is configured to bend between the first terminal end surface 304 and the second terminal end surface 306 and between the opposed first and second side surfaces 308 and 310. The anatomical implant template 300 can be configured to bend at one or more bending locations along at least a portion of the anatomical implant template 300 between the first and second terminal end surfaces 304 and 306 and between the opposed first and second side surfaces 308 and 310. In at least some embodiments, the anatomical implant template 300 can bend continuously along at least a portion, up to an entirety, of the anatomical implant template 300 that extends between the first and second terminal end surfaces 304 and 306 and between the opposed first and second side surfaces 308 and 310.

For example, the anatomical implant template 300 can include a bending location that extends along at least a portion, up to an entirety, of the length L1 of the anatomical implant template 300 and along at least a portion, up to an entirety, of the width W1 of the anatomical implant template 300. Alternatively, the anatomical implant template 300 can include a plurality of bending locations, each of which extends continuously along a different portion of the anatomical implant template 200 between the first terminal end surface 304 to the second terminal end surface 306 and between the first side surface 308 to the second side surface 310. Alternatively still, the bending locations can be defined by discrete bending points that are spaced from one another between the first and second terminal end surfaces 304 and 306 and/or between the opposed first and second side surfaces 308 and 310. For example, the anatomical implant template 300 can be configured to bend along discrete points that are spaced from one another along (i) a line that extends between the first and second terminal end surfaces 304 and 306 and/or (ii) a line that extends between the opposed first and second side surfaces 308 and 310. For illustrative purposes, FIG. 10 shows the anatomical implant template 300 having one bend; however, the user can bend the template body 202 so as to have more than one bend.

The anatomical implant template 300 is configured to bend at the bending locations so as to change the anatomical implant template 300 from a first configuration to a second configuration. In at least some embodiments, the first configuration is an initial or pre-operative configuration, and the second configuration is a subsequent or post-operative configuration, where the subsequent or post-operative configuration can conform more closely to the desired, post-operative curvature or contour of the at least one anatomical body than the initial or pre-operative configuration.

In the first configuration, the anatomical implant template 300 extends from the first terminal end surface 304 to the second terminal end surface 306 along a first path P1, and in the second configuration, the anatomical implant template 300 extends from the first terminal end surface 304 to the second terminal end surface 306 along a second path P2, different from the first path P1. The first and second paths P1 and P2 can be parallel to one or more of the midline ML1, the upper surface 312, and the lower surface 314. The first path P1 has a first curvature, and the second path P2 has a second curvature, different from the first curvature.

Moreover, in the first configuration, the anatomical implant template 300 extends from the first side surface 308 to the second side surface 310 along a third path P3, and in the second configuration, the anatomical implant template 300 extends from the first side surface 308 to the second side surface 310 along a fourth path P4, different from the third path P3. The third and fourth paths P3 and P4 can be parallel to one or more of the midline ML2, the upper surface 312, and the lower surface 314. The third path P3 has a third curvature, and the fourth path P4 has a fourth curvature, different from the third curvature.

It will be understood that the first to fourth paths P1 to P4 shown in FIGS. 9 and 10 are merely examples and that, in practice, the first to fourth paths P1 to P4, and hence the first to fourth curvatures, can vary from that shown in FIGS. 9 and 10. The first and third paths P1 and P3 may extend along straight lines as shown or can define any suitable curvature. Further, the second and fourth paths P2 and P4 may extend along parabolic curves as shown or can define any other suitable curvature to match the curvature of the at least one anatomical body. In at least some embodiments, the anatomical implant template 300 is further configured to be bent at one or more of the bending locations so as to change the template body from the second configuration back to the first configuration, or to a third configuration that is different from both the first and second configurations.

The anatomical implant template 300 can be configured to bend along multiple planes. In particular, the anatomical implant template 300 can be configured to bend at each of the bending locations about an axis A of rotation that extends through the anatomical implant template 300, where the axis A of rotation can extend through the anatomical implant template 300 in any direction in a three dimensional space. For example, the axis A of rotation may extend through the anatomical implant template 300 at the bending location between the first and second terminal end surfaces 304 and 306 in a direction that is parallel to the first midline ML1. Thus, when the anatomical implant template 300 is bent about the axis A of rotation, the anatomical implant template 300 curves from the first side surface 308 to the second side surface 310 such that the first side surface 308 moves closer to the second side surface 310. As another example, the axis A of rotation may extend between the first and second side surfaces 308 and 310 in a direction that is parallel to the second midline ML2. Thus, when the anatomical implant template 300 is bent about the axis of rotation, the anatomical implant template 300 curves from the first terminal end surface 304 to the second terminal end surface 306, and the first terminal end surface 304 moves closer to the second terminal end surface 306. Additionally or alternatively, the axis A of rotation may extend between any pair of the first terminal end surface 304, the second terminal end surface 306, the first side surface 308, and the second side surface 310 at any angle between the first and second midlines ML1 and ML2. For example, the axis A of rotation may extend through the anatomical implant template 300 from the first terminal end surface 304 to the second side surface 310 so as to bend the anatomical implant template 300 at that the upper right-hand corner of the anatomical implant template 300.

For illustrative purposes, FIG. 10 shows one point 316 that defines a peak of the curvature of the anatomical implant template 300, where the peak 316 is at a geometric center of the anatomical implant template 300. The anatomical implant template 300 has first and second axes A1 and A2 of rotation that extend through the peak 316. The first axis A1 of rotation is coincident with the second midline ML2 and the second axis A2 of rotation is coincident with the first midline ML1. As a result, the anatomical implant template 300 is bent such that (i) the anatomical implant template 300 curves from the first side surface 308 to the second side surface 310 so as to bring the first and second side surfaces 308 and 310 closer together, and (ii) anatomical implant template 300 curves from the first terminal end surface 304 to the second terminal end surface 306 so as to bring the first and second terminal end surfaces 304 and 306 closer together.

Note that the anatomical implant template 300 can additionally or alternatively define at least one peak that is not at the geometric center of the anatomical implant template 300 and can further define more than one peak so as to have more than one curve. For example, the anatomical implant template 300 can have a peak that is located on either side of the first midline ML1 and/or on either side of the second midline ML2. Thus, the anatomical implant template 300 can be bent about axes of rotation that are not coincident with the first and/or the second midlines ML1 and/or ML2. In other words, the anatomical implant template 300 can bend on either side of the first midline ML1 and/or on either side of the second midline ML2. The anatomical implant template 300 may have multiple such second axes of rotation between the first and second terminal end surfaces 304 and 306 and/or between the first and second side surfaces 308 and 310.

In the first configuration, the anatomical implant template 300 can define a first radius R1 of curvature at the point 316, where the first radius R1 of curvature lies in a first plane that is coincident with, or parallel to, the first axis A1 of rotation and/or perpendicular to the second axis A2 of rotation. Further, in the first configuration, the anatomical implant template 300 can also define a third radius R3 of curvature at the point 316, where the third radius R3 of curvature lies in a second plane that is coincident with, or parallel to, the second axis A2 of rotation and/or perpendicular to the first axis A1 of rotation. In the second configuration, the anatomical implant template 300 defines a second radius R2 of curvature at the point 316, where the second radius R2 of curvature lies in the first plane, and the second radius R2 of curvature is different from the first radius R1 of curvature. In the second configuration, the anatomical implant template 300 can also define a fourth radius R4 of curvature at the bending location 316, where the fourth radius R4 of curvature lies in the second plane, and the fourth radius R4 of curvature is different from the third radius R3 of curvature.

Figure 11:
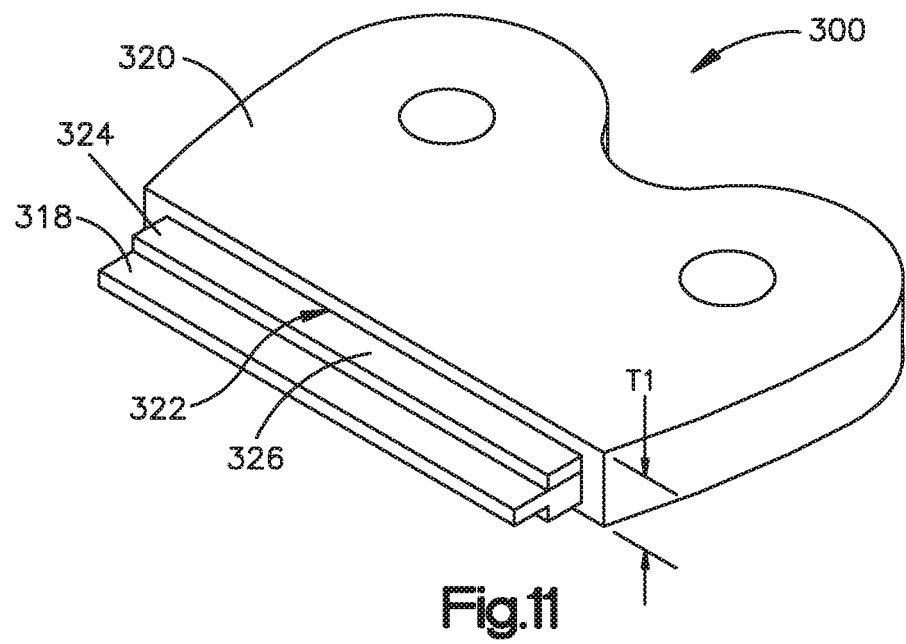
FIG. 11 shows a cross-sectional view of the anatomical implant template of FIGS. 9 and 10 according to one embodiment.
Figure 12:
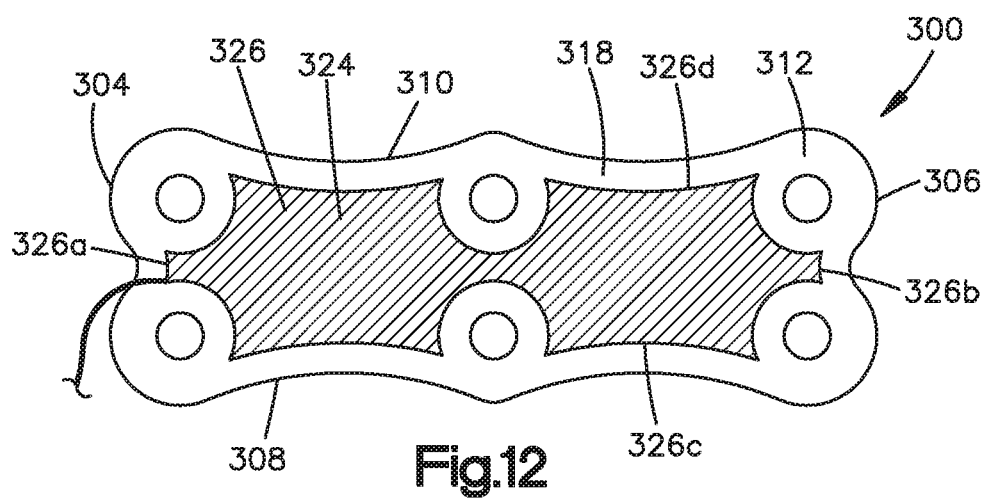
FIG. 12 shows a top view of the anatomical implant template of FIGS. 9 and 10 according to another embodiment.

Turning now to FIGS. 11 to 13, various embodiments of the anatomical implant template 200 of FIGS. 9 and 10 are shown. In each embodiment, the anatomical implant template 300 includes a template body 302 and at least one sensor 324 coupled to the template body 302. The template body 302 is configured to bend so as to change the anatomical implant template 300 from the first configuration to the second configuration. The at least one sensor 324 is configured to output at least one sensor signal from which the curvature of the anatomical implant template 300 in the second configuration can be ascertained.

The template body 302 includes a flexible body 318 that extends along, or substantially parallel to, (i) the midline ML1 between the first and second terminal end surfaces 304 and 306, and (ii) the midline ML2 between the first and second side surfaces 308 and 310. The flexible body 318 can extend from the first terminal end surface 304 toward the second terminal end surface 306, and terminate at or before the second terminal end surface 306. Similarly, the flexible body 318 can extend from the second terminal end surface 306 toward the first terminal end surface 304, and terminate at or before the first terminal end surface 304. Alternatively, the template body 302 can extend along a portion or portions of the anatomical implant template 300 between the first and second terminal end surfaces 304 and 306, and terminate before one or both of the first and second terminal end surfaces 304 and 306.

In other words, the template body 302 can have a first terminal end and a second terminal end. The first terminal end of the template body 302 can be coincident with the first terminal end surface 304 of the implant template 300 or can be located between the first and second terminal end surfaces 304 and 306. Similarly, the second terminal end of the template body 302 can be coincident with the second terminal end surface 304 or can be located between the first and second terminal end surfaces 304 and 306.

The flexible body 318 can extend from the first side surface 308 toward the second side surface 310, and terminate at or before the second side surface 310. Similarly, the flexible body 318 can extend from the second side surface 310 toward the first side surface 308, and terminate at or before the first side surface 308. Alternatively, the template body 302 can extend along a portion or portions of the anatomical implant template 300 between the first and second side surfaces 308 and 310, and terminate before one or both of the first and second side surfaces 308 and 310.

In other words, the template body 302 can have a first side and a second side. The side of the template body 302 can be coincident with the first side surface 308 of the implant template 300 or can be located between the first and second side surfaces 308 and 310. Similarly, the second side of the template body 302 can be coincident with the second side surface 308 or can be located between the first and second side surfaces 308 and 310.

The flexible body 318 can include any suitable malleable material or combination of malleable materials that permits the template body 302 to be conformed to the desired post-operative contour of the at least one anatomical body. The malleable material or combination of materials may include one or more of a metal such as annealed aluminum, a metal alloy such as Nitinol, and a polymer. The flexible body 318 can include a plastically-deformable material configured to maintain the template body 302 in the second configuration. Alternatively, or in addition, the flexible body 318 can include an elastically-deformable material configured to return the template body 302 to the first configuration from the second configuration.

With continuing reference to FIGS. 9 to 13, the anatomical implant template 300 supports at least one sensor 324 along or substantially parallel to (i) the midline ML1 between the first and second terminal end surfaces 304 and 306 and (ii) the midline ML2 between the first and second side surfaces 308 and 310. The at least one sensor 324 is configured output at least one sensor signal from which the shape of the anatomical implant template 300 in the second configuration can be ascertained. The at least one sensor 324 can include a sensor body 326 having a first terminal sensor end 326a, a second terminal sensor end 326b spaced from the first terminal sensor end 326a along the midline ML1, a first sensor side 326c, a second sensor side 326d spaced from the first sensor side 326c along the midline ML2, an upper surface 326e, and a lower surface 326f space from the upper surface along a direction that is perpendicular to both the first and second midlines ML1 and ML2. The lower surface 326 can be configured to face the at least one anatomical body. In at least some embodiments, the sensor body 326 can be elongate from the first terminal sensor end 326a to the second terminal sensor end 326b.

The sensor body 326 can extend from the first terminal end surface 304 of the implant template 300 toward the second terminal end surface 306 of the implant template 300, and terminate at or before the second terminal end surface 306. Additionally or alternatively, the sensor body 326 can extend from the second terminal end surface 306 toward the first terminal end surface 304, and terminate at or before the first terminal end surface 304. The sensor body 326 can extend from the first side surface 308 toward the second side surface 310, and terminate at or before the second side surface 210. Additionally or alternatively, the sensor body 326 can extend from the second side surface 310 toward the first side surface 308, and terminate at or before the first side surface 310. Thus, the sensor body 326 can extend along a portion or portions of the template body 302 between the first and second terminal end surfaces 304 and 306 such that the sensor body 226 terminates at or before one or both of the first and second terminal end surfaces 304 and 306 and between the first and second side surfaces 308 and 310 such that the sensor body 326 terminates at or before one or both of the first and second side surfaces 308 and 310.

The sensor body 326 can be coupled to the template body 302 such that at least a portion of the sensor body 326 is aligned with at least one of the bending locations along a direction that is perpendicular to the upper and lower surfaces 312 and 314 of the implant template 300. Accordingly, when the template body 302 is bent at the at least one bending location, the sensor body 326 is also bent at the at least one bending location.

Alternatively or in addition, the at least one sensor 324 can include a plurality of discrete sensor bodies 326 spaced from one another between the first and second terminal end surfaces 304 and 306 and between the first and second side surfaces 308 and 310. When discrete sensor bodies 326 are employed, changes in the shape of the template body 302 between the discrete sensors can be determined through extrapolation. In either case, the elongate sensor body 326 and/or the plurality of discrete sensor bodies 326 can be coupled to the template body 302 so as to be aligned with at least one of the bending locations such that the at least one sensor 324 bends at the at least one bending location. Alternatively, the sensor body 324 and/or the plurality of discrete sensor bodies 324 can be coupled to the template body 302 so as to be positioned between (i) at least one of the bending locations and (ii) another of the bending locations, the first terminal end surface 304, the second terminal end surface 306, the first side surface 308, or the second side surface 310 such that a position of the at least one sensor 324 changes relative to the at least one of the bending locations as the template body 302 is bent about the at least one of the bending locations.

The at least one sensor 324 can include any suitable sensor or combination of sensors that can sense the shape of the template body 324 in the second configuration. The at least one sensor 220 can be an active sensor that actively transmits a signal or a passive sensor. The at least one sensor 324 can include, for example, one or more position sensors that measure absolute position of the template body 302 in the second configuration or relative position such as displacement of the template body 302 from the first configuration to the second configuration. In at least some embodiments, the at least one sensor 324 can include one or more piezoelectric sensors as described above in relation to the at least one sensor 220. The piezoelectric sensors can be used to measure changes in or more of pressure, strain, and force, and convert these measured changes into at least one sensor signal. In at least some embodiments, the at least one sensor 324 can include an optical sensor as described above in relation to the at least one sensor 220. The at least one sensor signal can be, for example, an electrical signal or an optical signal.

Turning now to FIG. 11, an embodiment is shown in which the template body 302 includes a flexible body 318 and can optionally include a protective covering 320. The flexible body 318 defines a plate that extends between the first terminal end surface 304 and the second terminal end surface 306 of the template body 302 and between the first side surface 308 and the second side surface 310.

The protective covering 320 can cover at least a portion of the flexible body 318 between the first and second terminal end surfaces 304 and 306 and between the first and second side surfaces 308 and 310. Further, the protective covering can cover the first and second terminal end surfaces 304 and 306 and the first and second side surfaces 308 and 310. The protective covering 320 has an inner surface that defines a channel 322 that extends at least partially through the protective covering 320. The flexible body 318 and the at least one sensor 324 are sized to be received in the channel 322 such that the at least one sensor 324 is supported between the flexible body 318 and at least a portion of the protective covering 320. In alternative embodiments, the template body 320 can define a channel that extends through the flexible body 318, such that the at least one sensor 324 is received in the channel and coupled to the flexible body 318.

With continued reference to FIG. 11, the at least one sensor 324 includes a flexible sensor body 326 that is planar so as to define a thin plate or sheet that extends between the first and second terminal end surfaces 304 and 306 of the template body 302 and/or between the first and second side surfaces 308 and 310. Thus, the sensor body 326 can extend along a portion or along a substantial entirety of the template body 302. Further, the sensor body 326 can be coupled to the template body 302 such that a portion of the sensor body 326 is aligned with at least one, up to all, of the bending locations of the anatomical implant template 300. Accordingly, when the template body 302 is bent at the at least one bending location, the sensor body 236 is also bent at the at least one bending location. The at least one sensor 324 can be configured to sense bending at each location along a surface of the sensor body 326.

Alternatively or in addition, the at least one sensor 324 can include a sensor grid, rather than a continuous elongate sensor, the sensor grid covering at least a portion of the surface of the flexible body 318. The sensor grid can include a plurality of sensor columns, each extending between the first and second terminal end surfaces 304 and 306, and a plurality of sensor rows, each extending between the first and second side surfaces 308 and 310. Each sensor row and/or each sensor column can include an elongate sensor or a plurality of discrete sensors spaced from one another. When discrete sensors are employed, changes in the shape of the elongate sensor body between the discrete sensors can be determined through extrapolation. In either case, the sensor body 326 and the plurality of discrete sensors 326 can be coupled to the template body 302 so as to be aligned with at least one of the bending locations such that the at least one sensor 324 bends at the at least one bending location. Alternatively, the sensor body 326 and/or the plurality of discrete sensors 326 can be positioned between (i) at least one of the bending locations and (ii) another of the bending locations, the first terminal end surface 304, the second terminal end surface 306, the first side surface 308, or the second side surface 310 such that a position of the at least one sensor 324 changes relative to the at least one of the bending location as the template body 302 is bent about the at least one of the bending locations.

Turning now to FIG. 12, an embodiment is shown in which the at least one sensor 324 is supported on the upper surface 312 of the anatomical implant template 300. In this embodiment, the at least one sensor 324 is planar so as to define a thin strip or sheet that is mounted onto the upper surface 312. For instance, the at least one sensor 324 can be a sticker that is adhered to the upper surface 312 or can be a strip that is adhered to the surface via an adhesive. The at least one sensor 324 can be removeably coupled to the flexible body 318 such that the flexible body 318 can be reused after cleaning as with conventional templates. Further, the at least one sensor 324 can be disposable or can be configured to survive cleaning such that the at least one sensor 324 can be reused.

Referring to FIG. 13, an embodiment is shown in which the anatomical implant template 300 defines at least one channel 330 that extends into the template body 302 toward the lower surface 314 such that the at least one channel 330 is open opposite the lower surface 314. To accommodate each of the first and second channels 330a and 330b, the template body 300 can optionally include at least one protrusion 332 that extends above the upper surface 312 of the template body 302, where the at least one channel 330 extends into the at least one protrusion 332.

The at least one channel 330 can define a first channel 330a that is elongate between the first terminal end surface 304 and the second terminal end surface 306. The at least one channel 330 can further define a second channel 330b that is elongate between the first side surface 308 and the second side surface 310. The first and second channels 330a and 330b can overlap or intersect one another, and the first and second channels 330a and 330b can define any suitable cross-sectional shape, such as (without limitation) a circle as shown, an oval, a square, or a rectangle.

As shown in FIG. 14, the at least one sensor 324 can include a pair of overlapping elongate sensors 324a and 324b. The first sensor 324a can be elongate from a first terminal sensor end 326a to a second terminal sensor end 326b, and the second sensor 324b can be elongate from the first sensor side 326c to the second sensor side 326c. The first and second sensors 324a and 324b can be press-fit into the first and second channels 330a and 330b, respectively. Alternatively, as shown in FIG. 15, the at least on sensor 324 can be a sheet sensor having first and second sensors 324a and 324b.

Returning to FIGS. 9 and 10, the anatomical implant template 300 is configured to communicate the at least one sensor signal to a computing device such as computing device 104 of FIG. 1 via a wired or wireless connection. The at least one sensor can be configured to communicate the at least one sensor signal directly to the computing device. Alternatively, the anatomical implant template 300 can include at least one transmitter 334 coupled to the template body 302 and configured to communicate the at least one sensor signal. The at least one transmitter 334 can be supported anywhere by the template body 302, and can be supported such that the at least one transmitter 334 does not bend with the template body 302. The at least one transmitter 334 can include a wireless transmitter configured to wirelessly communicate the at least one sensor signal to the computing device. Further, the at least one transmitter 334 can include a power supply coupled to the template body 302, where the power supply is configured to power the at least one transmitter 334. Alternatively, the at least one transmitter 334 can be powered by a power supply that is not coupled to the template body 302, such as a power supply that is coupled to a receiver such as an RFID receiver that senses the at least one sensor signal from a sensor coupled to the template body 302. In the case of a wired connection, the anatomical implant template 300 can be coupled to a cable that carries the at least one sensor signal from the anatomical implant template 300 to the computing device.

Referring to FIG. 16, a simplified flow diagram is shown of a method 400 of operating the anatomical implant template 102 of FIG. 1 according to one embodiment. In step 402, the anatomical implant template 102 is positioned along the at least one anatomical body. The positioning includes bending the template body at one or more bending locations as described above. For example, the positioning can include bending the anatomical implant template 102 between the first terminal end surface and the second terminal end surface of the template body so as to change the template body from the first configuration to the second configuration that conforms more closely to a contour or curvature of the at least one anatomical body than the first configuration. The anatomical implant template 102 can be bent so as to avoid bending the anatomical implant template 102 at one or more securement locations that are used to secure the anatomical-fixation implant to the at least one anatomical body (e.g., at locations where the anatomical implant template 102 is attached to a pedicle screw or adjacent to apertures in the anatomical implant template 102 that receive bone screws).

Bending the anatomical implant template 102 at the one or more bending locations can include bending at least one sensor that is aligned with the one or more bending locations. Alternatively, bending the anatomical implant template 102 at the one or more bending locations can include bending the anatomical implant template 102 such that at least one sensor spaced from the one or more bending locations is repositioned relative to the one or more bending locations. The anatomical implant template 102 can be plastically deformed such that the anatomical implant template 102 remains in the second configuration, or the anatomical implant template 102 can be elastically deformed such that the anatomical implant template 102 returns to the first configuration after a bending force is removed.

Bending of the anatomical implant template 102 can be performed before positioning the anatomical implant template along the at least one anatomical body, can be performed after positioning the anatomical implant template along the at least one anatomical body, or can be performed concurrently with positioning the anatomical implant template along the at least one anatomical body. Step 402 can yet further include securing the anatomical implant template to the at least one anatomical body with at least one fixation device. The at least one fixation device can include, for example, at least one bone anchor such as a bone screw and/or hook. The at least one bone anchor can include a rod-receiving recess to receive the anatomical implant template 102 in the case that the anatomical implant template 102 defines a rod shape. In embodiments in which the anatomical implant template 102 defines a plate, the at least one fixation device can include at least one screw or pin that is received through a hole defined in the anatomical implant template 102 to secure the anatomical implant template 102 to bone underlying the anatomical implant template 102.

In step 404, the at least one sensor coupled to the anatomical implant template 102 generates at least one signal 114 from which the shape of the anatomical implant template 102 in the second configuration can be ascertained. For example, in embodiments where an optical sensor is used, the optical sensor can generate at least one sensor signal by modifying an input light source. The at least one signal 114 can be indicative of the shape of the anatomical implant template 102 in the second configuration. For example, the at least one signal 114 can be indicative of absolute position of the anatomical implant template 102 in the second configuration or relative position such as displacement of the anatomical implant template 102 from the first configuration to the second configuration.

Generating the at least one sensor signal can occur concurrently with bending of the anatomical implant template 102 or after bending of the anatomical implant template 102 has finished. The at least one sensor signal can be generated in any manner described above or in any suitable alternative manner. In some embodiments, the anatomical implant template 102 can include a processor coupled to the template body that processes the at least one sensor signal. For example, the processor can perform at least one of compression, amplification, filtering, and conversion of the signal from one format to another. The conversion can include, for example, analog-to-digital conversion, optical-to-electronic conversion In step 406, the anatomical implant template 102 communicates the at least one sensor signal to the computing device 104. As described above, the communicating can include communicating the at least one sensor signal via a wireless or wired connection. Further, the anatomical implant template 102 can communicate the at least one sensor signal directly from the at least one sensor to the computing device 104, such that the at least one sensor can be considered to be a transmitter, or can communicate the at least one sensor signal to the computing device 104 via a transmitter that is separate from the at least one sensor and that is coupled to the anatomical implant template 102. The data obtained from the at least one sensor signal can be used immediately in or near the operating room to fabricate the anatomical-fixation implant 110 or can be used at a later time to fabricate the anatomical-fixation implant 110 either in or near the operating room or at a location that is remote from the operating room. Alternatively or additionally, the data obtained from the at least one sensor signal can be aggregated for subsequent and on-going analysis to improve patient outcomes.

Turning now to FIG. 17, a simplified flow diagram is shown of a method 500 of manipulating the anatomical-fixation implant 110 of FIG. 1 according to one embodiment. In step 502, the computing device 104 receives data that can be used to determine a desired post-operative shape for the anatomical-fixation implant 110. For example, the data can include the at least one signal 114 from the anatomical implant template 102 as described above, where the at least one signal 114 carries information from which the shape of the anatomical implant template 102 in the second configuration can be ascertained. The at least one signal 114 can be received via a wireless connection or via a wired connection including one or more cables. Alternatively, the computing device 104 can receive data obtained through another manner from which the desired post-operative shape of the anatomical implant template 102 can be ascertained. For example, the data can be obtained using imagery or scans of an implant template at the surgical site. In such embodiments, the implant template can include at least one marker, such as at least one reflective marker, that can be used to identify the shape of the anatomical implant template. Alternatively, the imagery can identify the locations of screws or other fixation devices implanted at the surgical site, where the screws or other fixation devices will be used to attach the anatomical-fixation implant 110 to the surgical site. In this case, the desired post-operative shape can be determined by modeling a line, such as a best fit line, through the screws or fixation devices.

In step 504, the computing device 104 generates implant bending signals 116 that are used to bend the anatomical fixation implant 110. In at least some embodiments, the computing device 104 can generate a 3-dimensional computer model of the anatomical implant template or anatomical-fixation implant in the second configuration. Further, the computer model can be manipulated to allow for added correction not present in the anatomical-implant template, for example, when the surgeon determines that added correction is appropriate for a specific patient's conditions and/or indications. The implant bending signals 116 can then be generated from the computer model or the manipulated computer model.

In step 506, the computer-controlled bending machine 106 obtains implant bending signals that correspond to a shape of the anatomical-fixation implant in a desired post-operative configuration, the shape having at least one bent region. For example, the computing device 104 can communicate the implant bending signals 116 to the computer-controlled bending machine 106, which receives the anatomical-fixation implant 110 in a first or pre-operative implant configuration 108. The anatomical-fixation implant 110 in the pre-operative implant configuration 108 can be, for example, a rigid piece of stock material that is not bendable by hand. The computer-controlled bending machine 106 may cut the anatomical-fixation implant 110 to a desired length, or the anatomical-fixation implant 110 may be precut to the desired length. The computer-controlled bending machine 106, which can be situated inside the operating room or at a location other than inside the operating room, bends the anatomical-fixation implant 110 from the first implant configuration 108 to a second or post-operative implant configuration 112 using the implant bending signals 116 in step 506. The post-operative configuration 112 conforms to the curvature of the anatomical fixation template 102, and consequently to the curvature of the at least one anatomical body. The computer-controlled bending machine 106 bends the anatomical-fixation implant 110 such that the shape of the anatomical-fixation implant 110 changes in a manner similar to that described above in relation to the anatomical implant templates of FIGS. 2 to 15. For example, the computer-controlled bending machine 106 bends the anatomical-fixation implant 110 about one or more bending locations on the anatomical-fixation implant 110 and about one or more axes of rotation in a manner similar to that described above in relation to FIGS. 2 to 8 in the case of that the anatomical-fixation implant 110 includes a rod and as described above in relation to FIGS. 9 to 15 in the case that the anatomical-fixation implant 110 includes a plate.

In step 508, the anatomical implant template 102 is removed from the at least one anatomical body, which can include bending the template body at the one or more bending locations so as to change the template body from the second configuration back to the first configuration. Note that step 508 can alternatively be performed prior to step 506 as long as the anatomical implant template 102 is maintained in the post-operative configuration. In step 510, the anatomical-fixation implant 110 in the post-operative configuration 112 is implanted by positioning the anatomical-fixation implant 110 along the at least one anatomical body and fixing the anatomical-fixation implant 110 to the at least one anatomical body via one or more fixation devices. The anatomical-fixation implant 110 may be positioned in a manner similar to that described above in relation to the anatomical implant templates of FIGS. 2 to 15. For example, the anatomical-fixation implant 110 can be positioned in one or more of the sagittal plane and the coronal plane. As another example, the anatomical-fixation implant 110 can extend across a plurality of anatomical bodies, such as at least two vertebrae or at least one vertebra and the skull or sacrum.

Fixing the anatomical-fixation implant 110 to the at least one anatomical body can include manipulating the at least one anatomical body to achieve a desired curvature of the at least one anatomical body, and can be performed before or during the positioning the anatomical-fixation implant 110 along the at least one anatomical body.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure. Further, it should be appreciated, that the term substantially indicates that certain directional components are not absolutely perpendicular to each other and that substantially perpendicular means that the direction has a primary directional component that is perpendicular to another direction.

What is claimed is:

1. A method of determining a shape for an anatomical implant, the method comprising steps of:
   positioning an anatomical implant template along at least one anatomical body, the anatomical implant template defining first and second opposed terminal ends, and including a flexible body that extends between the first and second opposed terminal ends, the flexible body having an external surface at least partially covered by a protective covering, and an internal surface opposite the external surface, the internal surface defining a channel therethrough that supports at least one sensor therein;
   bending the template from a first configuration, whereby the anatomical implant template extends along a first path from the first terminal end to the second terminal end, to a second configuration, whereby the anatomical implant template extends from the first terminal end to the second terminal end along a second path different from the first path, wherein when the anatomical implant template is in the second configuration, the anatomical implant template conforms more closely to a curvature of the at least one anatomical body as compared to when the template is in the first configuration; and
   causing the at least one sensor to generate a signal having information from which a shape of the anatomical implant template in the second configuration can be ascertained; and
   causing a transmitter supported by the flexible body to wirelessly communicate the signal to a computing device.

2. The method of claim 1, comprising generating, at the computing device, a computer model of the anatomical implant template in the second configuration from the at least one sensor signal.

3. The method of claim 2, comprising bending an anatomical-fixation implant based on the computer model of the anatomical implant template so to conform the anatomical-fixation implant to the curvature of the at least one anatomical body.

4. The method of claim 3, comprising bending the anatomical-fixation implant with a computer-controlled bending machine.

5. The method of claim 1, wherein the positioning comprises implanting the anatomical implant template onto the at least one anatomical body.

6. The method of claim 1, wherein the positioning comprises manipulating the at least one anatomical body to achieve the curvature of the at least one anatomical body.

7. The method of claim 1, wherein the positioning comprises manipulating the at least one anatomical body and the anatomical implant template to achieve the curvature of the at least one anatomical body.

8. The method of claim 1, wherein the transmitter is powered by a power supply supported by the flexible body.

9. The method of claim 1, wherein the sensor is a piezoelectric sensor.

10. The method of claim 1, wherein the flexible body is made of metal.

11. A method of manipulating an anatomical-fixation implant, the method comprising steps of:
    receiving at least one signal from a wireless transmitter of an anatomical implant template having first and second opposed terminal ends, and a flexible body that extends between the first and second opposed terminal ends, the flexible body having an external surface at least partially covered by a protective covering, and an internal surface opposite the external surface, the internal surface defining a channel therethrough that supports at least one sensor therein, the at least one signal including information from which a shape of at least one bent region of the flexible body can be ascertained;
    generating implant bending signals that correspond to the at least one signal; and
    bending the anatomical-fixation implant based on the implant bending signals so as to include the at least one bent region.

12. The method of claim 11, comprising bending the anatomical-fixation implant with a computer-controlled bending machine.

13. The method of claim 12, further comprising positioning the bent anatomical-fixation implant along the at least one anatomical body.

14. The method of claim 13, wherein the positioning comprises securing the anatomical-fixation implant to the at least one anatomical body with a fixation device.

15. The method of claim 13, wherein the positioning comprises manipulating the at least one anatomical body to achieve the curvature of the at least one anatomical body.

16. The method of claim 11, wherein the anatomical-fixation implant comprises a first terminal end, and a second terminal end spaced from the first terminal end, and the bending comprises bending the anatomical-fixation implant from a first configuration, wherein the anatomical-fixation implant extends from the first terminal end surface to the second terminal end surface along a first path having a first curvature, to a second configuration, wherein the anatomical-fixation implant extends from the first terminal end surface to the second terminal end surface along a second path having a second curvature, different from the first curvature.

* * * * *